United States Patent [19]
Lee et al.

[11] Patent Number: 5,951,973
[45] Date of Patent: *Sep. 14, 1999

[54] USE OF INTERLEUKIN-4 (IL-4) TO TREAT RHEUMATOID ARTHRITIS

[75] Inventors: Frank Lee; Takashi Yokota; Ken-ichi Arai, all of Palo Alto; Timothy Mosmann, Atherton; Donna Rennick, Los Altos, all of Calif.

[73] Assignee: Schering Corporation, Kenilworth, N.J.

[21] Appl. No.: 08/466,543

[22] Filed: Jun. 6, 1995

Related U.S. Application Data

[60] Division of application No. 06/843,958, Mar. 25, 1986, Pat. No. 5,552,304, which is a continuation-in-part of application No. 06/799,668, Nov. 19, 1985, abandoned.

[51] Int. Cl.$^6$ .......................... A61K 38/20; C07K 14/54; C12N 15/24
[52] U.S. Cl. ................................ 424/85.2; 514/2; 514/8; 514/12; 514/825; 514/885; 530/351; 435/69.52; 435/252.3; 435/320.1; 435/471; 435/325
[58] Field of Search .................................. 424/85.1, 85.2; 514/2, 8, 12, 825, 885; 530/351; 435/69.52, 252.3, 320.1, 471, 325

[56] References Cited

U.S. PATENT DOCUMENTS 5,236,705   8/1993   Hamilton et al. ...................... 424/85.2

FOREIGN PATENT DOCUMENTS 0218431   9/1986   European Pat. Off. .

OTHER PUBLICATIONS

Howard et al., "Identification of a T Cell–Derived B Cell Growth Factor Distinct from Interleukin 2" *J. Exp. Med.*, vol. 155, pp. 914–923 (1982).
Yoshizaki et al., "Induction of Proliferation and Ig Production in Human B Leukemic Cells by Anti–Immunoglobulins and T Cell Factors" *The Journal of Immunology*, vol. 128, pp. 1296–1301 (1982).
Farrar et al., "Biochemical and Physiocochemical Characterization of Mouse B Cell Growth Factor: A Lymphokine Distinct from Interleukin–2" *The Journal of Immunology*, vol. 131, pp. 1838–1842 (1983).
Howard et al., "Regulation of B–Cell Growth and Differentiation by Soluble Factors" *Ann. Rev. Immunol.*, vol. 1, pp. 207–333 (1983).
Maizel et al., "Long–term Growth of Human B Cells and Their Use in a Microassay for B–Cell Growth Factor" *Proc. Natl. Acad. Sci.*, vol. 80, pp. 5047–5051 (1983).
Okada et al., "B Cell Growth Factors and B Cell Differentiation Factor from Human T Hybridomas" *J. Exp. Med.*, vol. 157, pp. 583–590 (1983).
Butler et al., "Characterization of Monoclonal B Cell Growth Factor (BCGF) Produced by a Human T–T Hybridoma" *The Journal of Immunology*, vol. 133, pp. 251–255 (1984).

Kishimoto, "Factors Affecting B–Cell Growth and Differentiation" *Ann. Rev. Immunol.*, vol. 3, pp. 133–157 (1985).
Mehta et al., "Purification of Human B Cell Growth Factor" *The Journal of Immunology*, vol. 135, pp. 3298–3302 (1985).
Ohara et al., "Partial Purification of Murine B Cell Stimulatory Factor (BSF–1)" *The Journal of Immunology*, vol. 135, pp. 2518–2523 (1985).
Oliver et al., "B–Cell Growth Factor (B–Cell Growth Factor I or B–Cell–Stimulating Factor, Provisional 1) is a Diff. Factor for Resting B Cells . . ." *Proc. Natl. Acad. Sci.*, vol. 82, pp. 2465–2467 (1985).
Rabin et al., "B–Cell Stimulatory Factor 1 Activates Resting B Cells" *Proc. Natl. Acad. Sci.*, vol. 82, pp. 2935–2939 (1985).
Sideras et al., "Secretion of $IgG_1$ Induction Factor by T Cell Clones and Hybridomas" *Eur. J. Immunol.*, vol. 15, pp. 586–593 (1985).
Sideras et al., "Partial Biochemical Characterization of $IgG_1$–Inducing Factor" *Eur. J. Immunol.*, vol. 15, pp. 593–598 (1985).
Thompson et al., "T Cell–Derived B Cell Growth Factor(s) Can Induce Stimulation of Both Resting and Activated B Cells" *The Journal of Immunology*, vol. 134, pp. 369–374 (1985).
Vivetta et al., "Serological, Biochemical, and Functional Identity of B Cell–Stimulatory Factor 1 and B Cell Differentiation Factor for $IgG_1$" *J. Exp. Med.*, vol. 162, pp. 1726–1731 (1985).
Noma et al., "Cloning of cDNA Encoding the Murine $IgG_1$ Induction Factor by a Novel Strategy Using SP6 Promoter" *Nature*, vol. 319, pp. 640–646 (1986).
Sahasrabuddhe et al., "Purification and Partial Characterization of Human Intracellular B Cell Growth Factor" *Lymphokine Research*, vol. 5, pp. 127–140 (1986).
O'Garra et al., *Immunology Today*, vol. 9, pp. 45–54 (1988).
Lewontin, ch. 3 in *The Genetic Basis of Evolutionary Change*.
Vogel et al., pp. 373–378 of *Human Genetics*.
Hunt et al., pp. 67–82 of *Atlas of Protein Sequence and Structure 1972*.
Sensabaugh, *Isozymes*, vol. 11, pp. 137–154 (1983).
Weatherall et al., *Cell*, vol. 16, pp. 467–479 (1979).
Nagata et al., *Nature*, vol. 287, pp. 401–408 (1980).
Lee et al., *Proc. Natl. Acad. Sci.*, vol. 82, p. 4360 (1985).

(List continued on next page.)

*Primary Examiner*—Prema Mertz
*Attorney, Agent, or Firm*—Immac J. Thampoe; Edwin Ching

[57] ABSTRACT

A method of treating rheumatoid arthritis comprising administering human Interleukin-4 (IL-4) to an individual afflicted with the disease. The IL-4 is administered with a pharmaceutically acceptable carrier in a dose ranging from 1 μg to 100 mg.

10 Claims, 9 Drawing Sheets

OTHER PUBLICATIONS

Wong et al., *Science,* vol. 228, pp. 810–815 (1985).
Burgess et al., *Blood,* vol. 69, pp. 43–51 (1987).
Fuse et al., *Nucleic Acids Research,* vol. 12, pp. 9323–9331 (1984).
Ullrich et al., *Nature,* vol. 303, pp. 821–825 (1983).
Cantrell et al., *Proc. Natl. Acad. Sci.,* vol. 82, pp. 6250–6254 (1985).
Sharma et al., *Science,* vol. 235, pp. 1489–1492 (1987).
Hirano et al., *Nature,* vol. 324, pp. 73–76 (1986).
Brandis et al., *Genetic Engineering,* vol. 8, pp. 299–316 (1986).
Hart et al. (1995) Immunology vol. 84 pp. 536–542.
Allen et al. (1993) J. of Immunology, vol. 151 pp. 4344–4351.
Mentz et al. (1994) J. of Biol. Chem. vol. 269, No. 33, pp. 21322–21329.

```
            10         20         30         40         50
TTAGCATCTC TTGATAAACT TAATTGTCTC TCGTCACTGA CGCACAGAGC TATTG ATG GGT CTC
                                                             MET Gly Leu 70                      85                 100                 115
AAC CCC CAG CTA GTT GTC ATC CTG CTC TTC TTT CTC GAA TGT ACC AGG AGC CAT
Asn Pro Gln Leu Val Val Ile Leu Leu Phe Phe Leu Glu Cys Thr Arg Ser His 130                 145                 160
ATC CAC GGA TGC GAC AAA AAT CAC TTG AGA GAG ATC ATC GGC ATT TTG AAC GAG
Ile His Gly Cys Asp Lys Asn His Leu Arg Glu Ile Ile Gly Ile Leu Asn Glu 175                 190                 205                 220
GTC ACA GGA GAA GGG ACG CCA TGC ACG GAG ATG GAT GTG CCA AAC GTC CTC ACA
Val Thr Gly Glu Gly Thr Pro Cys Thr Glu MET Asp Val Pro Asn Val Leu Thr 235                 250                 265                 280
GCA ACG AAG AAC ACC ACA GAG AGT GAG CTC GTC TGT AGG GCT TCC AAG GTG CTT
Ala Thr Lys Asn Thr Thr Glu Ser Glu Leu Val Cys Arg Ala Ser Lys Val Leu 295                 310                 325
CGT ATA TTT TAT TTA AAA CAT GGG AAA ACT CCA TGC TTG AAG AAG AAC TCT AGT
Arg Ile Phe Tyr Leu Lys His Gly Lys Thr Pro Cys Leu Lys Lys Asn Ser Ser 340                 355                 370                 385
GTT CTC ATG GAG CTG CAG AGA CTC TTT CGG GCT TTT CGA TGC CTG GAT TCA TCG
Val Leu MET Glu Leu Gln Arg Leu Phe Arg Ala Phe Arg Cys Leu Asp Ser Ser 400                 415                 430
ATA AGC TGC ACC ATG AAT GAG TCC AAG TCC ACA TCA CTG AAA GAC TTC CTG GAA
Ile Ser Cys Thr MET Asn Glu Ser Lys Ser Thr Ser Leu Lys Asp Phe Leu Glu 445                 460                 475             488         498
AGC CTA AAG AGC ATC ATG CAA ATG GAT TAC TCG TAG TACTGAGCCA CCATGCTTTA
Ser Leu Lys Ser Ile MET Gln MET Asp Tyr Ser  •

508        518        528        538        548        558
ACTTATGAAT TTTTAATGGT TTTATTTTTA ATATTTATAT ATTTATAATT CATAAAATAA 568        578
AATATTTGTA TAATGTAACA GAAAAAA
```

FIG. 1A

```
                10         20         30         40         50         60
        GATCGTTAGC TTCTCCTGAT AAACTAATTG CCTCACATTG TCACTGCAAA TCGACACCTA TTA 78                      93                     108
        ATG GGT CTC ACC TCC CAA CTG CTT CCC CCT CTG TTC TTC CTG CTA GCA TGT GCC
        MET Gly Leu Thr Ser Gln Leu Leu Pro Pro Leu Phe Phe Leu Leu Ala Cys Ala 123                    138                    153                    168
        GGC AAC TTT GTC CAC GGA CAC AAG TGC GAT ATC ACC TTA CAG GAG ATC ATC AAA
        Gly Asn Phe Val His Gly His Lys Cys Asp Ile Thr Leu Gln Glu Ile Ile Lys 183                    198                    213
        ACT TTG AAC AGC CTC ACA GAG CAG AAG ACT CTG TGC ACC GAG TTG ACC GTA ACA
        Thr Leu Asn Ser Leu Thr Glu Gln Lys Thr Leu Cys Thr Glu Leu Thr Val Thr 228                    243                    258                    273
        GAC ATC TTT GCT GCC TCC AAG AAC ACA ACT GAG AAG GAA ACC TTC TGC AGG GCT
        Asp Ile Phe Ala Ala Ser Lys Asn Thr Thr Glu Lys Glu Thr Phe Cys Arg Ala 288                    303                    318                    333
        GCG ACT GTG CTC CGG CAG TTC TAC AGC CAC CAT GAG AAG GAC ACT CGC TGC CTG
        Ala Thr Val Leu Arg Gln Phe Tyr Ser His His Glu Lys Asp Thr Arg Cys Leu 348                    363                    378
        GGT GCG ACT GCA CAG CAG TTC CAC AGG CAC AAG CAG CTG ATC CGA TTC CTG AAA
        Gly Ala Thr Ala Gln Gln Phe His Arg His Lys Gln Leu Ile Arg Phe Leu Lys 393                    408                    423                    438
        CGG CTC GAC AGG AAC CTC TGG GGC CTG GCG GGC TTG AAT TCC TGT CCT GTG AAG
        Arg Leu Asp Arg Asn Leu Trp Gly Leu Ala Gly Leu Asn Ser Cys Pro Val Lys 453                    468                    483
        GAA GCC AAC CAG AGT ACG TTG GAA AAC TTC TTG GAA AGG CTA AAG ACG ATC ATG
        Glu Ala Asn Gln Ser Thr Leu Glu Asn Phe Leu Glu Arg Leu Lys Thr Ile MET 498                    513                          535        545        555
        AGA GAG AAA TAT TCA AAG TGT TCG AGC TGA ATATTTTAAT TTATGAGTTT TTGATAGCTT
        Arg Glu Lys Thr Ser Lys Cys Ser Ser •

565        575        585        595        605        615
        TATTTTTTAA GTATTTATAT ATTTATAACT CATCATAAAA TAAAGTATAT ATAGAATCTA AAA
```

FIG. 1B

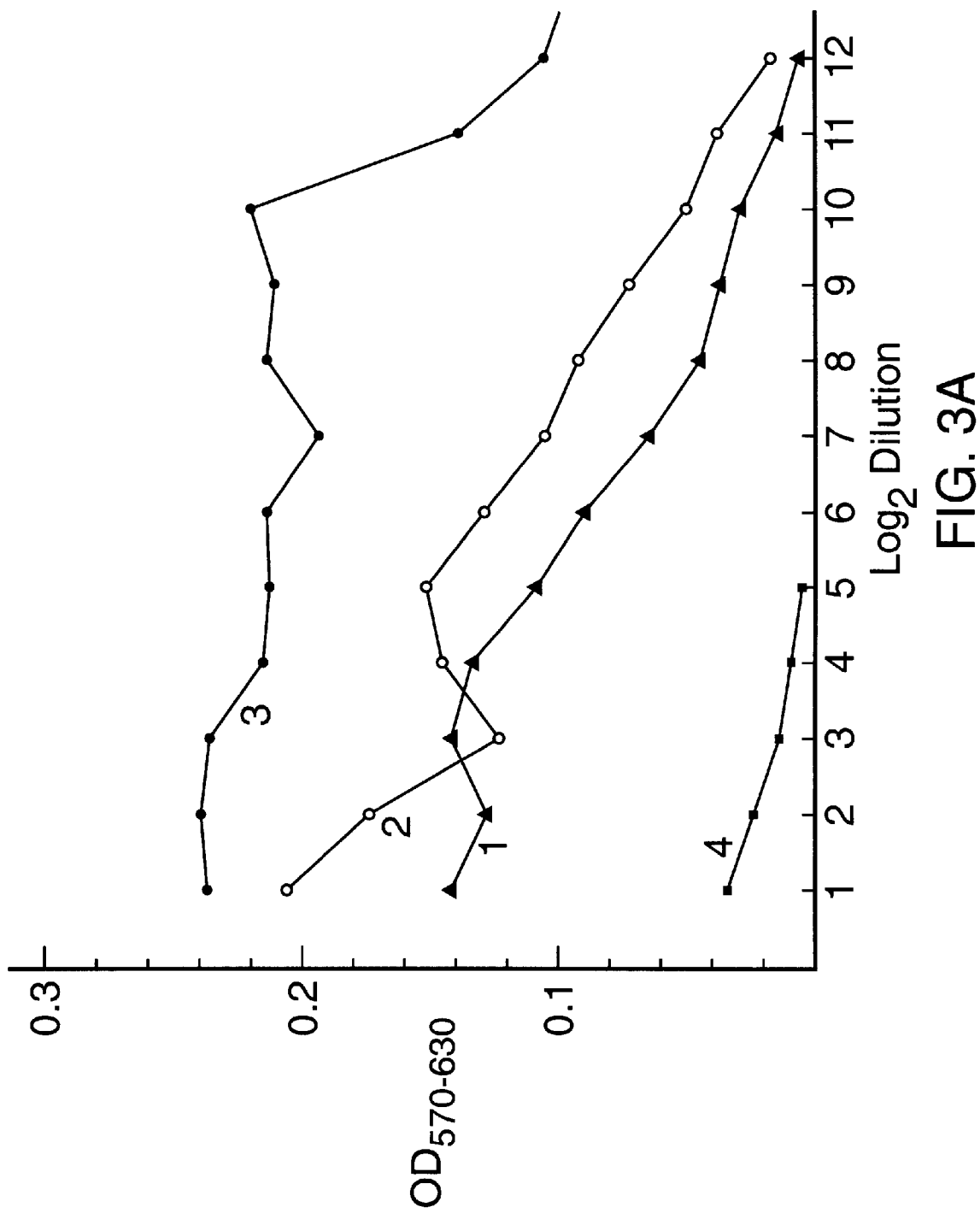

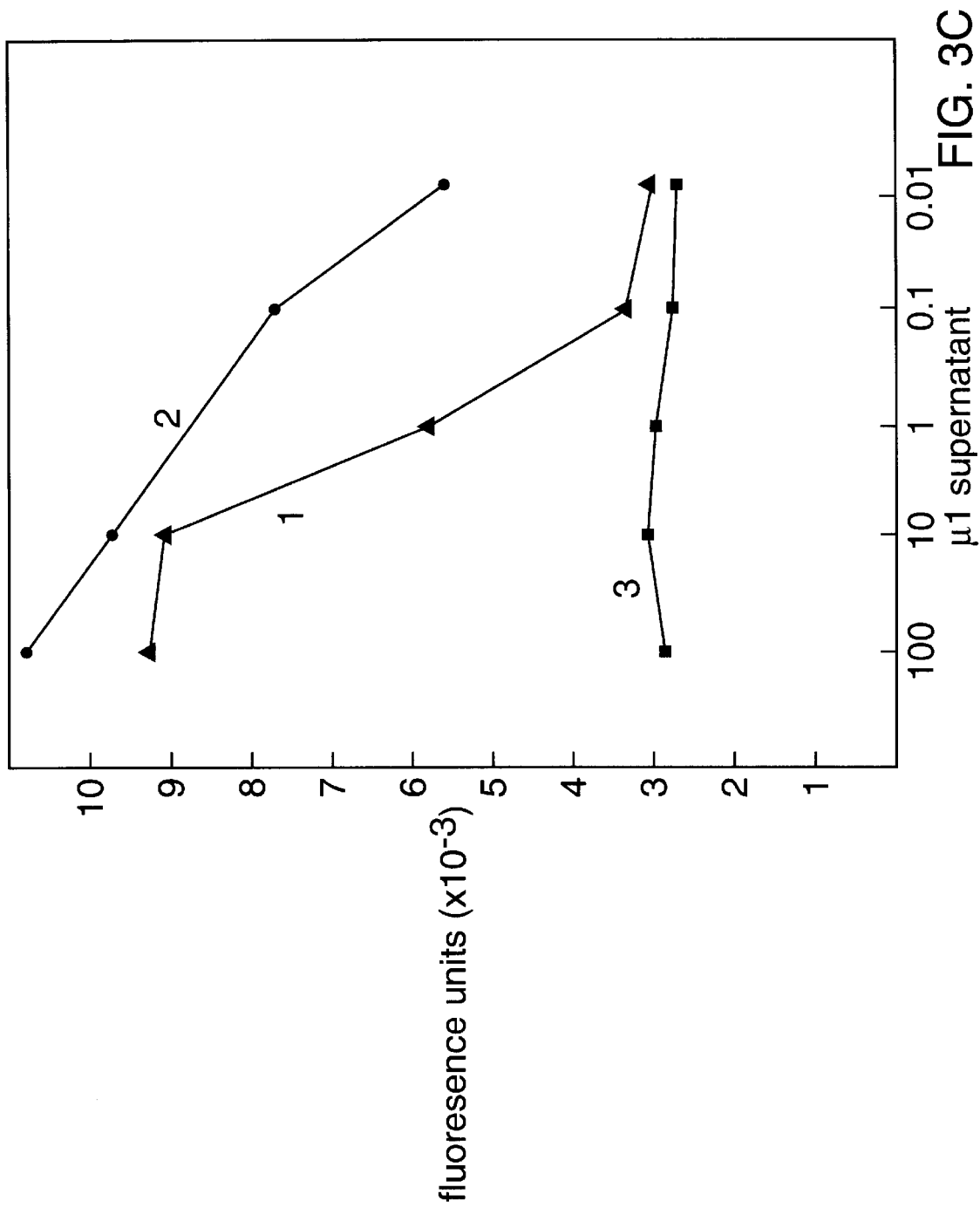

USE OF INTERLEUKIN-4 (IL-4) TO TREAT RHEUMATOID ARTHRITIS

This is a divisional of application U.S. Ser. No. 06/843,958, filed on Mar. 25, 1986 now U.S. Pat. No. 5,552,304, which is a C-I-P of Ser. No. 799,688, filed Nov. 19, 1985, now abandoned.

FIELD OF THE INVENTION

This invention relates generally to the application of recombinant DNA technology to elucidate the control mechanisms of the mammalian immune response and, more particularly, to the isolation of nucleic acid clones coding for polypeptides capable of exhibiting B-cell, T-cell, macrophage and mast cell stimulatory activity, as well as colony stimulating factor enhancing activity.

BACKGROUND OF THE INVENTION

Recombinant DNA technology refers generally to the technique of integrating genetic information from a donor source into vectors for subsequent processing, such as through introduction into a host, whereby the transferred genetic information is copied and/or expressed in the new environment. Commonly, the genetic information exists in the form of complementary DNA (cDNA) derived from messenger RNA (mRNA) coding for a desired protein product. The carrier is frequently a plasmid having the capacity to incorporate cDNA for later replication in a host and, in some cases, actually to control expression of the cDNA and thereby direct synthesis of the encoded product in the host.

This technology has progressed extremely rapidly in recent years and a variety of exogenous proteins have been expressed in a variety of hosts, but obtaining any desired novel cDNA clone remains an uncertainty. By way of example, some of the eukaryotic proteins produced by recombinant DNA technology include: proinsulin (Naber, S. et al., Gene 21:95–104 [1983]); interferons (Simon, L. et al., Proc. Natl. Acad. Sci. U.S.A., 80:2059–2062 [1983] and Derynck, R. et al., Nucl. Acids Res. 1:1819–1837 [1983]); growth hormone (Goeddel, D., et al., Nature 281:544–548 [1979]); a human T-cell growth factor (Taniguichi, T. et al., Nature 302:305–310 (1983)); and a granulocyte/macrophage cellular growth factor (G/M-CSF) (Miyatake, S. et al., EMBO J. 4:2561–2568 (1985)). These publications and other reference materials cited hereafter have been included to provide additional details on the background of the pertinent art and, in particular instances, the practice of the invention, and are all incorporated herein by reference.)

For some time, it has been documented that the mammalian immune response is based on a series of complex cellular interactions, called the "immune network." Recent research has provided new insights into the inner workings of this network. While it remains clear that much of the response does, in fact, revolve around the network-like interactions of lymphocytes, macrophages, granulocytes and other cells, immunologists now generally hold the opinion that soluble proteins (e.g., the so-called "lymphokines") play a critical role in controlling these cellular interactions. Thus, there is considerable interest in the isolation, characterization, and mechanisms of action of cell modulatory factors, an understanding of which should yield significant breakthroughs in the diagnosis and therapy of numerous disease states.

Lymphokines apparently mediate cellular activities in a variety of ways. They have been shown to support the proliferation, growth and the differentiation of the pluripotential hematopoietic stem cells into the vast number of progenitors composing the diverse cellular lineages responsible for the immune response. These lineages often respond in a different manner when lymphokines are used in conjunction with other agents.

Cell lineages important to the immune response include two classes of lymphocytes: B-cells, which can produce and secrete immunoglobulins (proteins with the capability of recognizing and binding to foreign matter to effect its removal), and T-cells of various subsets that secrete lymphokines and induce or suppress the B-cells and some of the other cells (including other T-cells) making up the immune network.

Another important cell lineage is the mast cell (which has not been positively identified in all mammalian species)—a granule-containing connective tissue cell located proximal to capillaries throughout the body, with especially high concentrations in the lungs, skin, and gastrointestinal and genitourinary tracts. Mast cells play a central role in allergy-related disorders, particularly anaphylaxis as follows: when selected antigens crosslink one class of immunoglobulins bound to receptors on the mast cell surface, the mast cell degranulates and releases the mediators (e.g., histamine, serotonin, heparin, kinans, prostaglandins, etc.) which cause allergic reactions, e.g., anaphylaxis, as well as others.

Research to better understand (and thus potentially treat therapeutically) various immune disorders has been hampered by the general inability to maintain in vitro cells of the immune system. Immunologists have discovered that culturing these cells can be accomplished through the use of T-cell and other cell supernatants, which contain various growth factors, such as some of the lymphokines.

The detection, isolation and purification of these factors is extremely difficult, being frequently complicated by the complexity of the supernatants they are typically located in, the divergencies and cross-overs of activities of the various components in the mixtures, the sensitivity (or lack thereof) of the assays utilized to ascertain the factors' properties, and the frequent similarity in the range of molecular weights and other characteristics of the factors.

Clarification of these issues requires additional structural data, e.g., substantially full-length sequence analysis of the molecules in question. Protein sequencing offers, of course, a possible means to solve the problem, but it is very difficult work experimentally and often can provide neither completely accurate nor full-length amino acid sequences. Moreover, having the capability of making bulk quantities of a polypeptide exhibiting activity on the cells of the immune system will greatly facilitate the study of the biology of those and other cells, e.g., by minimizing the necessity of relying on lectin conditioned media for stimulating cell growth. Accurate and complete sequence data on any immune protein will also serve to simplify the search for other immunological factors. Finally, additional information on any lymphokine will help in evaluating the roles of the various growth factors and cells of the immune network and thus provide insight into the entire immune system—with the concomitant therapeutic benefits.

Thus, there exists a significant need for extensive nucleotide sequence data on the DNAs coding for, and amino acid sequences of, proteins exhibiting immune cell growth or stimulatory activity, as well as a simple and economic method of making substantial and essentially pure quantities of such materials. The present invention fulfills these needs.

DESCRIPTION OF ADDITIONAL RELEVANT REFERENCES

Metcalf, D. "The Hematopoeitic Colony Stimulating Factors," Elsevier, Amsterdam (1984), provides an overview of research concerning lymphokines and various growth factors involved in the mammalian immune response. Yung, Y.-P., et al., J. Immunol. 127:794 (1981) describe the partial purification of the protein of approximately 35 kd exhibiting mast cell growth factor (MCGF) activity and its separation from interleukin-2 (IL-2), also known as T-cell growth factor (TCGF). Nabel, G., et al., Nature 291:332 (1981) report an MCGF exhibiting a molecular weight of about 45 kd and a pI of about 6.0. Clark-Lewis, I. and Schrader, J., J. Immunol. 127:1941 (1981) describe a protein having mast cell like growth factor activity that exhibits a molecular weight of about 29 kd in phosphate-buffered saline and about 23 kd in 6M guanidine hydrochloride, with a pI of between about 4–8 but of about 6–8 after neuraminidase treatment. Murine IL-2 and interleukin-3 (IL-3) have been partially characterized biochemically by Gillis, S., et al., J. Immunol. 124:1954–1962 (1980) and Ihle, J., et al., J. Immunol. 129:2431–2436 (1982), respectively, with IL-2 having an apparent molecular weight (probably as a dimer) of about 30–35 kd and IL-3 having a molecular weight of about 28 kd. Human IL-2 apparently has a molecular weight of about 15 kd and is described by Gillis, S., et al., Immun. Rev. 63:167–209 (1982). Comparison between IL-3 and MCGF activities of T-cell supernatants have been reported by Yung Y. and Moore, M., Contemp. Top. Mol. Immunol. 10:147–179 (1985) and Rennick, D., et al., J. Immunol. 134:910–919 (1985).

B-cell stimulatory factor (BSF-1) has been separated physically from IL-2 and shown to have a molecular weight of about 11 kd and about 15 kd, with pI values of 6.4–6.7 and 7.4, respectively, by Farrar, J., et al., J. Immunol. 131:1838–1842 (1982). Ohara, J. and Paul, W., Nature 315:333–336 describe a monoclonal antibody allegedly specific for murine BSF-1 and molecular weights for BSF-1 of 14 kd and 19–20 kd with a pI of 6.7. The existence of at least two distinct human B cell grow factors (BCGFs) has been suggested by others (see, Kishimoto, T., Ann. Rev. Immunol., 3:133–157 [1985]). Yoshizaki, K., et al. (J. Immunol. 130:1241–1246 (1983) showed that an IL-2 dependent helper T-cell clone (d4) produced a 50 KD BCGF distinct from a 15–20 KD BCGF isolated from PHA stimulated T-cells, and the two BCGF's showed a synergistic effect on the proliferation of anti-IgM-stimulated B cells. Also, a factor having synergistic colony stimulating factor activity and other activities was described by Kriegler, A., et al., Exp. Hematol. 12:844–849 (1984).

SUMMARY OF THE INVENTION

The present invention provides cDNA clones coding for immune modulating factor (IMF) polypeptides capable of exhibiting a broad spectrum of activities on mammalian hematopoietic cells, including B-cells, T-cells, granulocytes, macrophages and mast cells. Nucleotide sequences for two cDNA's and putative amino acid sequences for the associated polypeptides are shown in FIG. 1. The cDNA sequences can be integrated into various vectors, which in turn can direct the synthesis of the corresponding polypeptides in a variety of hosts, including eukaryotic cells, such as mammalian cells in culture.

More specifically, the invention provides a process for producing polypeptides exhibiting the desired activities, the process comprising the steps of:

a) forming a vector comprising a nucleotide sequence coding for one of the polypeptides, wherein the nucleotide sequence is capable of being expressed by a host containing the vector;

b) incorporating the vector into the host; and c) maintaining the host containing the vector under conditions suitable for expression of the nucleotide sequence into said polypeptides.

Preferably, the cDNA sequences are derived from T-cell mRNA sequences coding for the native polypeptides, and the host is an organism such as a eukaryotic, e.g., mammalian cell transfected or transformed with the vector. Further, the vector preferably comprises also a second nucleotide sequence capable of controlling expression of the nucleotide sequence for the polypeptide. This second sequence can include a promoter sequence, one or more intron sequences and a polyadenylation sequence, to permit, respectively, transcription, splicing and polyadenylation of the nucleotide sequences coding for the polypeptides. Particularly, when the host is a mammalian cell, such as a COS-7 monkey kidney cell (COS), the vector contains the promoter sequence of the Simian virus 40 (SV40) early region promoter and the polyadenylation sequence of the SV40 late region polyadenylation sequence.

The cDNA sequences of FIG. 1 are capable of hybridizing with other DNA sequences, such as DNA coding for other mammalian IMF's from cDNA or genomic libraries. Some of the cDNA sequences may contain information for a leader sequence.

The polypeptides of the present invention can be used to stimulate B-cells and to enhance T-cell, granulocyte and mast cell growth. When used in association with other immune-reactive agents, the activities of such agents are enhanced. Suitable pharmaceutical compositions can be prepared by adding the polypeptides, within or without other agents, to therapeutically compatible carriers.

Other features and advantages of the invention will become apparent from the following detailed description, which describes, in conjunction with the accompanying drawings and by way of example, the present invention.

BRIEF DESCRIPTION OF THE FIGURES

FIG. 1A shows a mouse cDNA insert which encodes mouse IL-4.

FIG. 1B shows a human IL-4 cDNA which encodes human IL-4.

Figure 2A:
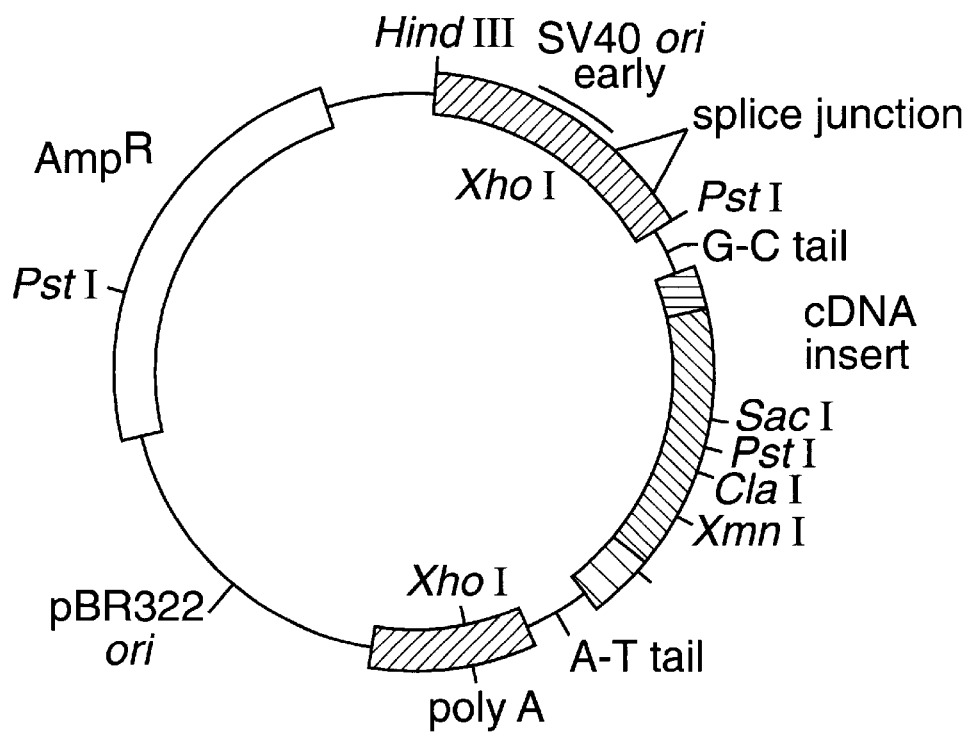
FIG. 2 depicts a map of an expression vector and cDNA insert of the present invention. (A) General diagram of pcD 2A-E3, a vector carrying a functional cDNA insert of the present invention. The cDNA insert extends from the GC tail to the AT tail and contains the indicated restriction endonuclease cleavage sites; the coding region is heavily shaded, and the noncoding regions are lightly shaded. The direction of transcription from the SV40 promoter is indicated by the arrow. (B) Restriction endonuclease cleavage map of the insert in clone 2A-E3 is shown.

Open circles, Human IL-2;

Open triangles, Mock COS supernatant;

Closed Squares, COS-Human (clone #46);

Open Squares, COS-Human (clone #125, oligo(dG) deleted); and

Closed circles, L cell-Human (clone #125, oligo(dG) deleted).

DESCRIPTION OF THE SPECIFIC EMBODIMENTS

In accordance with the present invention, cDNA clones are provided in substantially pure form, which clone that code for IMF polypeptides capable of exhibiting a broad activity spectrum on, for example, almost all hematopoietic cell lineages. The responses of each cell lineage can vary depending upon the environment, including the presence of additional lymphokines or other immune-reactive agents. After the cDNA sequences have been incorporated into replicable expression vectors, and the vectors transfected into an appropriate host (e.g., a mammalian cell culture), the expressed polypeptide or polypeptides can allow the expansion (usually species-specific) of T-cells, mast cells, and/or other receptive hematopoietic cell lineages (e.g., granulocytic) in vivo or in vitro.

The polypeptides produced in accordance with the present invention can exhibit synergistic activity in cells when the factors are combined with other im- mune reactive agents, such as increased mouse mast and granulocytic cell growth in conjunction with mouse IL-3 and increased production of granulocytic colonies when the polypeptides are present with granulocyte/macrophage colony stimulating factor (G/M-CSF) or granulocyte colony stimulating factor (G-CSF). These polypeptides can also induce Ia expression on resting B-cells, enhance IgG$_1$ and IgE secretion by B-cells, and promote the entry into S phase of B-cells activated by anti-IgM antibodies (see, Howard, M. et al., Immunol. Rev. 78:185 (1984), which is incorporated herein by reference). Moreover, the polypeptides can induce Ia induction on macrophages while limiting the macrophages' factor-dependent growth.

For purposes of describing this invention, IMF polypeptides are defined as the expression products, with or without processing of the nucleotide sequences (and allelic variants thereof) depicted in FIG. 1 and those of related mammalian genes. In accordance with the assays described herein, the activities of IMF polypeptides can include, but are not limited to, B-cell, T-cell, macrophage, and mast cell stimulation; and enhancement of colony stimulating factor activity in progenitor cells. Other activities include affinity for receptors on such cells and/or specific antibody preparations; antigenicity upon introduction into a foreign host; and the like. The processing may include: cleavage of 5 to 50 amino acids or more, typically 10–20 amino acids, from an internal fragment or from the amino or carboxy terminus of a polypeptide; disulfide bridging; glycosylation; and other protein processing well known to those skilled in the art.

Two exemplary, putative amino acid sequences based on mouse-and human-isolated nucleotide sequences of the present invention are shown in FIG. 1. FIG. 1A shows a mouse cDNA insert that contains a single open-reading frame consisting of 140 codons. Downstream of the putative initiation codon is a region rich in hydrophobic amino acids. It is likely, therefore, that the mature native form of secreted polypeptide begins with a histidine residue, and the preceding 20 amino acids constitute a leader region, which is subject to removal by proteolytic processing. Thus, in one embodiment, a polypeptide of the present invention would consist of about 120 amino acids, with a calculated molecular weight of approximately 14,000 daltons (unglycosylated). There appear to be three potential N-glycosylation sites (Asn-Xaa-Ser/Thr) (Neuberger, A. et al., Glycoproteins 5, 450–490, Elsevier Publishing Co., U.S.A. [1972]) at positions 61–63, 91–93, and 117–119, which could create a much higher and variable molecular weight depending upon the expression host, expression conditions, etc.

FIG. 1B shows another embodiment of the present invention, a human cDNA that contains 153 amino acid residues. Because this lymphokine also is a naturally secreted protein, a hydrophobic leader sequence would be expected to precede the sequence for the mature secreted form of the protein. Analysis of the hydrophobicity of the polypeptide and comparison with a proposed consensus sequence for the processing of signal peptides (Perlman, D. and Halverson, H., J. Mol. Biol. 167:391–409 [1983] suggest that cleavage of the precursor polypeptide could occur following the glycine residue at position 24. Thus, the mature polypeptide would be about 129 amino acid residues in length and begin with a histidine residue. The deduced Mr of the mature secreted protein is about 15,000 daltons. This molecular weight does not take into account potential post-translational glycosylation of the polypeptide, which is predicted by the presence of two potential N-glycosylation sequences (Asn-Xaa-Thr, or Asn-Xaa-Ser, at positions 62–64, and 129–131, respectively). Two of these positions appear naturally conserved between mice and humans.

A variety of methods may be used to prepare the cDNAs of the present invention. By way of example, total mRNA is extracted (e.g., as reported by Berger, S. et al., Biochemistry 18:5143:5149 [1979]) from cells (e.g., a nontransformed human T-cell source) producing polypeptides exhibiting the desired activity. The double-stranded cDNAs from this total mRNA can be constructed by using primer-initiated reverse transcription (Verme, I., Biochem. Biophys. Acta, 473: 1–38 [1977]) to make first the complement of each mRNA sequence, and then by priming for second strand synthesis (Land, H. et al., Nucleic Acids Res., 9: 2251–2266 [1981]). Subsequently, the cDNAs can be cloned by joining them to suitable plasmid or bacteriophage vectors (Rougeon, F. et al., Nucleic Acids Res., 2, 2365–2378 [1975]) or Scherer, G. et al., Dev. Biol. 86, 438–447 [1981]) through complementary homopolymeric tails (Efstratiadis, A. et al., Cell, 10, 571–585 [1977]) or cohesive ends created with linker segments containing appropriate restriction sites (Seeburg, P. et al., Nature, 270, 486–495 [1977] or Shine, J. et al., Nature, 270, 494–499 [1977]), and then transforming a suitable host. (See generally, Efstratiadis, A., and Villa-Kormaroff, L., "Cloning of double stranded cDNA" in Setlow, J. and Hollaender, A. (eds.) Genetic Engineering, Vol. 1, Plenum Publishing Corp., New York, U.S.A. [1982].)

A preferred method of obtaining the full-length cloned cDNAs of this invention is the procedure developed by H. Okayama and P. Berg (Mol. and Cell. Biol., 2: 161–170 [1982]). This method has the advantage of placing the cDNA inserts in a bacterial cloning vector at a position whereby the cDNA can also be directly translated and processed in mammalian cells. Briefly, the first cDNA strand is primed by polydeoxythymidylic acid covalently joined to one end of a linear plasmid vector DNA. The plasmid vector is then cyclized with a linker DNA segment that bridges one end of the plasmid to the 5' end of the cDNA coding sequence. By employing a DNA fragment containing the Simian Virus 40 (SV40) early region promoter and a linker containing a modified SV40 late region intron, the cDNA can be expressed in vitro in COS mouse cells without further modification. (See generally, Okayama, H. and Berg, P., Mol. and Cell. Biol., 3:280–289 [1983] and Jolly, D. et al., Proc. Nat. Acad. Sci. U.S.A., 80: 477–481 [1983], both of which are incorporated herein by reference.)

Once the cDNA library in the Okayama/Berg plasmid vector has been completed, the cDNA clones are collected, and random pools can be checked for the presence of the desired cDNAs by hybrid selection, translation, and assay (e.g., by measuring synergistic mast cell, or B cell or T-cell stimulatory activity in cell cultures, the existence of antigenic determinants, or other biological activities). Pools positive by these criteria can then be probed with an appropriate subtracted probe, e.g., cDNA from a B cell line and/or uninduced T-cell line. Thereafter, the positive, probed pools are divided into individual clones which are tested by transfection into a suitable host (such as a mammalian cell culture), and the host supernatant assayed for the desired activity. Positive clones are then sequenced.

The desired cDNA clones can also be detected and isolated by hybridization screening with appropriate mRNA samples (Heindell, H. et al., Cell, 15: 43–54 [1978]). Alternatively, the cDNA libraries can be screened by hybrid selection (Harpold, M. et al., Nucleic Acid Res., 5: 2039:2053 [1978] or Parnes, J. et al., Proc. Nat. Acad. Sci. U.S.A., 78:2253:2257 [1981]) or in Xenopus oocytes (Gurdon, J., Nature, 233: 177–182 [1971]). (See generally, Villa-Kormaroff, L. et al., Proc. Natl. Acad. Sci. U.S.A., 75:3727–3731 [1978].)

Once identified and obtained in substantially pure form, the cDNA's of the present invention can be inserted in their entirety or as fragments into any of a number of cloning and expression vehicles. Additional manipulations to create derived nucleotide sequence can include nucleotide base changes, additions and/or deletions to either reflect allelic variations within a species or otherwise modify the DNA sequences as described to allow for production, for example, of other polypeptides exhibiting one or more properties (e.g., cell proliferation, immunogenicity, etc.) of the native gene products. By way of example, those nucleotide sequences derived from the nucleotide sequences disclosed herein in accordance with the techniques well known to those skilled in the art, such as by chemical synthesis, come within the scope of the present invention.

Utilizing these general techniques, a number of lymphokine genes and/or the purification of proteins encoded by the genes, have been cloned by transfection into COS cells. Supernatants from transfected COS cells utilized in experiments described herein include for example: COS-IL-3 (Yokota, T. et al., Proc. Natl. Acad. Sci. U.S.A., 81:1070–1074) and COS-IL-2 (Yokota, T. et al., Proc. Natl. Acad. Sci. U.S.A., 82:68–72 (1985)). Co-pending applications relating to the cloning of various lymphokine genes include U.S. Ser. No. 539,050, filed Oct. 4, 1983 now abandoned; U.S. Ser. No. 590,867, filed Mar. 19, 1984 now U.S. Pat. No. 6,695,542; U.S. Ser. No. 658,183, filed Oct. 5, 1984 now abandoned; and U.S. Ser. No. 673,989, filed Nov. 20, 1984 now U.S. Pat. No. 6,546,733 and U.S. Ser. No. 799,699, filed Nov. 19, 1985 now abandoned. All of these publications and applications are incorporated herein by reference.

In further describing the procedures relating to preparing cDNA clones of the invention, the cellular source will be considered first, followed by general descriptions of the procedures for isolating mRNA coding for a protein exhibiting the activities of proteins of the present invention; the construction of a cDNA library containing the cDNA sequences; isolation of full-length cDNA clones in a plasmid vector and subsequent expression in mammalian cells; subcloning and expression in bacteria and yeast; and purification and formulation. A more detailed description of the entire experimental process will follow thereafter.

Cellular Sources

A preferred source of mRNA encoding the desired polypeptides are cells whose supernatants contain the B-cell, T-cell and mast cell stimulating activities, or other activities associated with the polypeptides of the present invention. One such line is the mouse T-cell line Cl.Lyl$^+$2$^-$/9 (A.T.C.C. Accession No. CRL8179) (Nabel, G. et al., Nature, 291:332–334 (1981)). In general, suitable T-cells can be obtained from a variety of sources, such as mammalian (e.g. human) spleen, tonsils and peripheral blood. T-cell clones, such as those isolated from peripheral blood T-lymphocytes, may also be used (see, *Research Monographs in Immunology,* eds. von Doehmer, H. and Haaf, V.; Section D: "Human T-Cell Clones", vol.8, pgs. 243–333; Elsevier Science Publishers, New York [1985]).

Isolation of mRNA and Construction of a cDNA Library

Total cellular mRNA can be isolated by a variety of well-known methods (e.g., Przybla, A. et al., J. Biol. Chem. 254: 2154–2158 [1979]), but the preferred method is the guanidinium-thiocyanate extraction procedure of Chirgwin et al. (Biochemistry, 18: 5294–5299 [1979]). If this method is used, approximately 10 µg of polyA mRNA, selected on columns of oligo (dT) cellulose, is obtained from 1–2×10$^8$ activated T-cells.

The cDNA library from the polyA$^+$ mRNA can best be constructed using the pcDVl vector-primer and the pLl linker fragment [available from the P-L Biochemicals Inc., Milwaukee, Wis.] according to procedures which result in greatly enriched full-length copies of mRNA transcripts (e.g. Okayama, H. and Berg, P., Mol. Cell Biol., 2, 161–170 [1982] and Mol. Cell Biol., 3, 280–289 [1983]). The plasmid vector, which contains SV40 early promoter and SV40 RNA processing signals, is designed to promote expression of the cloned cDNA segment in mammalian cells. If desired, the pcDV1 vector can be modified to contain an NsiI site at the previous location of the KpnI site (Yokota, T. et al., Proc. Natl. Acad. Sci. U.S.A., 82:68–72 (1985), which is incorporated herein by reference).

Using the Okayama and Berg procedure, the cyclized vector-cDNA preparation is transformed into a competent bacterial cell, such as *E. coli* MC1061 cells (Casadaban, M. and Cohen, S., J. Mol. Biol., 138: 179–207 [1980]) using calcium chloride (Cohen, S. et al., Proc. Nat. Acad. Sci. U.S.A., 69:2110–2114 [1972]). Starting with 5 μg of polyA+ RNA from ConA-stimulated T-cells, about 1×10$^5$ independent transformants can be obtained. Usually, about 10$^4$ clones are picked up individually and inoculated into wells of microtiter plates (Flow Laboratories Inc., McLean, Va.) containing 200 μl of L-broth, 50 μg/ml of ampicillin, and 7% DMSO. If desired, sublibraries based on the size of cDNA insert are prepared from total cDNA library as described by Okayama, H. Berg, P. (Mol. Cell Biol., 3, 280–299 [1983]). Briefly, plasmid DNA is digested with SalI, ClaI, and HindIII separately, and electrophoresed in a 1% agarose gel. After staining with ethidium bromide, the gel is sliced into 7 sections corresponding to cDNA insert sizes of 0 to 1, 1 to 2, 2 to 3, 3 to 4, 4 to 5, 5 to 6, and more than 6 kilobases (kb). DNA is extracted from each slice, recyclized with T4 DNA ligase, and used to transform MC1061. All nucleotide sequencing can be performed according to the procedure of Maxam, A. and Gilbert, W. (Methods Enzymol., 65:499–560 [1980] and Rubin, C. and Schnid, C., Nucl. Acids, Res., 8:4613–4619 [1980]), or a dideoxy chain termination protocol (Sanger, F. et al., Proc. Natl. Acad. Sci. U.S.A., 74:5463–5467 [1977] with supercoiled DNA templates.

DNA Transfections into Monkey Cells

Approximately 1×10$^6$ COS cells are seeded onto 60 mm plates the day prior to transfection. Transfections are best performed with 15 μg of plasmid DNA in 1.5 ml of DME containing 50 mM Tris.HCl, pH 7.4, and 400 μg/ml DEAE-Dextran (Pharmacia Fine Chemicals, Uppsala, Sweden). This solution is then removed after 4 hr and replaced with 2.0 ml DME+4% fetal calf serum. The medium is collected after 72 hr and assayed for the desired activities as described above. DNA transfections may be carried out in L-cells and a variety of other cell sources as well (see below).

Cellular Assays

Any of the traditional cellular assays may be utilized in accordance with established protocols well known to those skilled in the art. T-cell growth factor activity can be determined using factor-dependent T-cell lines; or peripheral blood blasts; B-cells growth factor activity can be determined using anti-IgM treated B-cells; in mice mast cell growth factor activity can be determined using mast cell lines; and colony stimulating factor activity can be determined using hematopoietic progeniter cells from bone marrow (or human cord blood) cultured, for example, in semi-solid medium. Proliferation can be determined either by incorporation of [$^3$H]thymidine or by a colorimetric assay as described in Rennick, D. M. et al. J. Immunol. 134:910–914 [1985]; and respectively, Mosmann, T., J. Immunol. Methods 65:55–63 [1983], both of which are incorporated herein by reference. The induction of Ia antigen on B cells can be performed as described in Roehm, N. W. et al., J. Exp. Med. 160:679–694 (1984). Briefly, the Ia positive phenotype is determined by staining with anti-I-A$^{bd}$ (D3.137.5.7.) or MK-d6 (anti-I-A$^d$) monoclonal antibodies and appropriate fluorescein-conjugated second antibodies. The analysis of stained cells is accomplished using a fluorescence activated cell sorter. The effect of test samples on the secretion of IgE and IgG$_1$ by cultures of LPS stimulated B cells is usually determined using isotype specific enzyme linked immunosorbant assays.

Isolation of Related Genes cDNA clones of the present invention can be used to identify and isolate nucleic acid sequences encoding related genes, such as from other mammals. Because of the frequent low degree of homology between homologous genes, the stringency of hybridization conditions must be adjusted to allow for cross-hybridization between sequences which may be only 70–80% homologous, or less.

Several different experimental protocols may be used to locate related genes. For example, the human Ck immunoglobulin light chain gene has been isolated using the corresponding mouse Ck gene as a probe (Heiter, P. et al., Cell 22:197–207 [1981]) and mouse transplantation antigen genes have been isolated by hybridization to DNA clones encoding their human counterparts (Steinnetz, T. et al., Cell 24: 125–134 [1981]). Both references are incorporated herein by reference.

For genomic DNA, a preferred method entails plating phage clones from a DNA library containing the homologous genes (Maniatis, T. et al., "Molecular Cloning, A Laboratory Manual, U.S.A. [1982]) at a density of 2×10$^4$ to 5×10$^4$ plaques per 150 mm plate in an appropriate host strain, such as E. coli LE392. Ten to twenty plates are generally sufficient.

After 10–12 hours' incubation at 37° C., the plates are refrigerated for two hours and then a 132 mm nitrocellulose filter is applied to the agar surface of each plate. The filter is allowed to remain in contact with the plate for at least five minutes, during which time the filters are keyed to the plates by puncturing with an ink-filled 22-gauge needle. The filters are then peeled from the plates and incubated successively for at least two minutes first in 250 ml of 0.1 N NaOH, 0.5 M NaCl; then in 250 ml of 0.5 M Tris.HCl pH 7.5, 1.5 M NaCl. The filters are dried on paper towels and then baked at 80° C. for 4–8 hours.

For hybridization, the filters are wetted in 1× SET (0.15 M NaCl, 30 mM Tris.HCl pH 8.0, 1 mM Na$_2$EDTA), then incubated in a solution of 3× SET, 5× Denhardt's (Denhardt, D. T., B.B.R.C. 23:641–646 [1966]), 10% dextran sulfate, 0.1% sodium dodecyl sulfate (SDS), and 50 μg/ml each poly (rA), poly (rC), and poly (rG), at 65° C. for 2 hrs (1.5–2 ml/filter) with constant agitation. This solution is then discarded, and the filters are hybridized with a nick-translated probe made from cDNA of the present invention (1×10$^8$ cpm) in the same solution (fresh), 1.5–2 ml/filter at 65°0 C. for 1 hour and then at 55° C. for 12–20 hours. The filters are then washed successively in 3× SET, 1× Denhardt's; 0.1% SDS; and 1× SET, 0.1% SDS (10–15 ml/filter) at 55° C. for one hour with gentle agitation. The filters are dried on paper towels, then autoradiographed for 12–24 hours with appropriate film and an intensifying screen. Hybridizing plaques are picked from agar plates with sterile Pasteur pipets, and each is expelled into 1 ml of 0.1 M NaCl, 0.01 M Tris.HCl pH 7.5, 10 mm MgCl$_2$, 100 μg/ml gelatin, with 50 μl of CHCl$_3$ added. After at least 4–8 hours in the cold, the phage from each plaque are rescreened at low density (2000–4000 plaques/150 mm plate) by a procedure identical to that described above.

Expression in E. Coli, in Yeast and in Cell Culture

Prokaryotes, such as E. coli, are very suitable for expression of the polypeptides of the present invention (see, for example, U.S. Pat. No. 4,338,397 and 4,411,994), provided glycosylation is not desired.

To obtain high expression levels, promoters should be utilized, such as the β-lactamase (penicillinase) and lactose promoter systems (Chang et al., Nature, 275:615 [1978]; Itakura et al., Science, 198: 1056 [1977]; Goeddel et al., Nature 281:544 [1979] or a tryptophan (trp) promoter system (Goeddel et al., Nucleic Acids Res., 8:4057 1980]) in conjunction with ribosome binding sequences.

Those skilled in the art will realize that not only prokaryotes but also eukaryotic microbes, such as yeast, may also be used in protein production. Saccharomyces cerevisiae is a preferred eukaryotic microorganism. Suitable promoting sequences in yeast vectors include the promoters for 3-phosphoglycerate kinase (Hitzeman et al., J. Biol. Chem., 255:12073–12080 [1980]) or other glycolytic enzymes (Hess et al., Adv. Enzyme Reg., 7:149–167 [1969]; Holland et al., Biochemistry, 17:4900–4907 [1978]). Other promoters that have the additional advantage of transcription controlled by growth conditions may be used. Basically any plasmid vector containing a yeast-compatible promoter, an origin of replication and termination sequences is suitable.

A preferred method of making polypeptides employing the cDNA's of the present invention utilizes the yeast mating pheromone α-factor secretory pathways (Julius, D. et al., Cell 32:839–852 [1983]). S. cerevisiae secretes mating-type specific oligopeptide pheromones. MATα cells secrete a-factor, which induces the growth arrest of MATα cells at G1 phase of the cell cycle (Thorner, J., *The Molecular Biology of the Yeast Saccharomyces,* Cold Spring Harbor Laboratory, New York [1981]; see particularly pages 153–180). The α-factor is initially synthesized as a larger precursor molecule consisting of an $NH_2$-terminal signal sequence of about 20 amino acids, followed by an additional 60 amino acid leader sequence and ending with four identical tandem repeats of the mature α-factor sequence. The repeats are separated from each other by six or eight amino acid spacers (Lys-Arg-Glu-Ala-Glu-Ala and Lys-Arg-Glu-Ala-Glu-[or Asp-]-Ala-Glu-Ala). This prepro-α-factor is cleaved at several specific sites. The first processing is the cleavage of the COOH-terminal side of the Lys-Arg pair of the spacer sequence catalysed by the KEX2 product (Julius et al., Cell 37:1075–1089 [1984]). A carboxypeptidase-B like enzyme cleaves at the $NH_2$-terminal side of the Lys-Arg pair. The final step is the removal of Glu-Ala or Asp-Ala pairs by diaminopeptidase, which is encoded by the STE13. Brake, J. et al., (Proc. Nat. Acad. Sci. U.S.A. 81:4642–4646 [1984]) have shown that the fusion of the sequence encoding mature human proteins to the first processing site allowed secretion of such proteins.

A 1.7 kb EcoRI fragment carrying the MFα1 gene (Kurjan, J. and Hershowitz, I., Cell. 30:933–943 [1982]) is cloned into the EcoRI restriction site of M13mp8 (Viera, J. and Messing, J., Gene 19:259–268 [1982]). In order to introduce a HindIII site after the lysine codon of the first spacer region, the synthetic oligonucleotide TCTTTTATC-CAAAGATACCC is hybridized to the single strand M13-Mfα1 DNA and the oligonucleotide primer extended by DNA polymerase I Klenow fragment. After S1 nuclease treatment, the DNA is cleaved with EcoRI and the fragment carrying the MFα1 promoter and leader sequence cloned into the EcoRI and filled-in HindIII restriction sites of PUC8 (Viera, J. and Messing, J. above). One plasmid with the desired structure can be isolated (designated PMFα4Δ1). The pMFα4Δ1 is cleaved with HindIII and partially filled in with DNA polymerase I Klenow fragment in the presence of dATP and DGPT. The DNA is treated with mung bean nuclease, and the oligonucleotide linker GCCTCGAGGC attached. The resultant plasmid (designated PMFα5) will have a StuI cleavage site immediately after the arginine codon, followed by the XhoI restriction site. An S. cerevisiae—E. coli shuttle vector (pTRP584) can be constructed as follows: the PstI-XbaI fragment carrying 2 μm plasmid replication origin (Broach, J. above) is cloned into the ClaI restriction site of PTRP56 (Miyajima et al., Mol. Cell. Biol. 4: 407–414 [1984]) and the StuI restriction site within the TRP1-ARS1 fragment converted into a PvuII restriction site by PvuII linker insertion. The KpnI restriction site in the original pTRP56 is converted to XhoI by the XhoI linker insertion. The general secretion vector pMFα8 is then obtained by insertion of the BglII-XhoI fragment of pMFα5 into the BamHI-XhoI restriction sites of pTRP584.

Those skilled in the art will realize that cDNA clones of the present invention may then be readily inserted into the pMFα8 vector and subsequently transformed in yeast for production of the desired polypeptides. By way of example, a BamHI fragment carrying an entire cDNA of the present invention is cloned into the BamHI restriction site of M13mp8 (Viera, J. and Messing, J., Gene 19:259–268 [1982]). In order to make a double stranded fragment carrying the mature protein coding sequence, a complementary oligonucleotide primer is constructed. This primer is then hybridized to a single stranded M13mp8 vector carrying cDNA of the present invention, and is extended by DNA polymerase I Klenow fragment. The double stranded DNA is cleaved with BamHI and then the single strand region is removed by mung bean nuclease. The double stranded fragment carrying the mature protein coding sequence of the present invention is then isolated and cloned into the StuI restriction site of the general secretion vector pMFχ8. This plasmid DNA (carrying the TRP1 gene) can be introduced into yeast cells by the lithium acetate method (Ito, H. et al., J. Bacteriol. 153:163–168 [1983]) and transformants selected in synthetic medium lacking tryptophan. Transformants are then grown in a common medium supplemented with 0.5% casamino acids. To harvest the yeast cells, they are first resuspended in phosphate-buffered-saline (PBS) containing 1 mM PMSF and then disintegrated by vigorous shaking with acid washed glass beads. Clear supernatant is obtained by centrifugation at 10,000 rpm for 15 min.

In addition to microorganisms, cell cultures derived from multicellular organisms (especially mammalian cells) may also be used as hosts. Examples of such useful host cell lines are HeLa cells, L cells, Chinese hamster ovary cell lines, and baby hamster kidney cell lines. Expression vectors for such cells ordinarily include, as necessary, an origin of replication, a promoter located in front of the gene to be expressed, along with any required ribosome binding sites, RNA splice sites, polyadenylation sites, and transcriptional terminator sequences. When used in mammalian cells, the expression vector often has control functions provided by viral material. For example, commonly used promoters are derived from polyoma, Adenovirus 2, and most frequently SV-40. (See, e.g., U.S. Pat. No. 4,399,216 and Ghuysen, D. and Fiers, W., J. of Mol. and Appl. Genetics 1:385–394 [1982].)

Purification and Formulations

The polypeptides of the present invention expressed in *E. coli,* in yeast or in other cells can be purified according to standard procedures of the art, including ammonium sulfate precipitation, fractionation column chromatography (e.g., ion exchange, gel filtration, electrophoresis, affinity chromatography, etc.) and ultimately crystallization (see generally "Enzyme Purification and Related Techniques," Methods in Enzymology, 22:233–577 [1977] and Scopes, R., *Protein Purification: Principles and Practice,* Springer-Verlag, New York [1982]). Once purified, partially or to homogeneity, the polypeptides of the invention may be used for research purposes, e.g., as a supplement to cell growth media (e.g., minimum essential medium Eagle, Iscove's modified Dulbecco Medium or RPMI 1640; available from Sigma Chemical Company, St Louis, Mo. and GIBCO Division, Chagrin Falls, Ohio) and as an antigenic substance for eliciting specific immunoglobulins useful in immunoassays, immunofluorescent stainings, etc. (See generally, *Immunological Methods,* Vols. I & II, Eds.

Lefkovits, I. and Pernis, B., Academic Press, New York, N.Y. [1979 & 1981]; and *Handbook of Experimental Immunology*, ed. Weir, D., Blackwell Scientific Publications, St. Louis, Mo. [1978].)

The polypeptides of the present invention may also be used in pharmaceutical compositions, e.g., to enhance natural defense against various infections. Thus, patients with rheumatoid arthritis, in need of a transplant, or with immunodeficiency caused by cancer chemotherapy, advanced age, immunosuppressive agents, etc., may be treated with such polypeptides. The compositions can selectively stimulate various components of the immune system, either alone or with other agents well known to those skilled in the art. In particular, the compositions may include other immune-reactive agents, such as lymphokines (e.g. IL-1, IL-2, etc.), any of the cloning stimulating factors, immunoglobulins, etc., in view of the demonstrated synergistic activities of the polypeptides of the present invention. The polypeptides will also find use in situations (in vivo or in vitro) in which enhanced cellular proliferation or immunoglobulin production is desired.

For preparing pharmaceutical compositions containing the polypeptides described by this invention, these polypeptides are compounded by admixture with preferably inert, pharmaceutically acceptable carriers. Suitable carriers and processes for their preparation are well known in the art (see, e.g., Remington's Pharmaceutical Sciences and U.S. Pharmacopeia: National Formulary, Mack Publishing Company, Easton, Pa. [1984]). The preferred course of administration is parenteral and can include use of mechanical delivery systems.

Preferably, the pharmaceutical composition is in unit dosage form. In such form, the preparation is subdivided into unit doses containing appropriate quantities of the active component. The quantity of active compound in a unit dose of preparation may be varied or adjusted from 1 $\mu$g to 100 mg, according to the particular application and the potency of the active ingredient. The composition can, if desired, also contain other therapeutic agents.

The dosages may be varied depending upon the requirement of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day.

The following experimental information and data are offered by way of example and not by way of limitation.

EXPERIMENTAL

Example I

This example demonstrates the isolation of a cDNA clone encoding polypeptides of the present invention that are active, in particular, on mouse cells.

A. Cloned Helper T Cells

1) A clone of T-cells Cl.Lyl$^+$2$^-$/9 (A.T.C.C. Accession No. CRL8179) expressing the Thy 1$^+$ Ly 1$^+$2$^-$phenotype is continuously maintained at 0.5×10$^{-5}$ cells/ml in Dulbecco's Modified Eagles medium (DME) with 10% heat-activated fetal calf serum, 5×10$^{-5}$ M 2-mercaptoethanol (2-ME), 2 mM glutamine, non-essential amino acids, and essential vitamins conditioned with 25% supernatants from Concanavalin A (Con A)-activated mouse Balb/c spleen cells.

2) Con A-activation of Cl.Lyl$^+$2$^-$/9 cells. The cells are cultured at 5×10$^5$/ml in DME with 4% heat-inactivated fetal calf serum, 5×10$^{-5}$ M 2-ME, 2 mM glutamine, non-essential amino acids, essential vitamins and 2 $\mu$g/ml Con A. After 12–14 hrs. incubation at 37° C. in 10% $CO_2$, the cell suspension is centrifuged at 1500 rpm for 10 minutes. The cell pellets are collected and frozen immediately at −70° C. The supernatants are filtered (Nalgene–0.22 microns) and stored at −20° C. as a source of growth factors. Aliquots of the supernatant are assayed for MCGF activity (see below) to verify the induction of the line by the Con A treatment.

B. Cellular Assays

1) TCGF Assay: T-cell growth factor activity was determined by [$^3$H]thymidine incorporation with the use of HT-2 T-cells as described in Nabel, G. et al., Proc. Natl. Acad. Sci. U.S.A., 78:1157 (1981), which is incorporated herein by reference. HT-2 cells were cultured at 5×10$^3$ cells/well (Falcon microtiter trays) in modified DME, 4% FCS, and varied concentrations of test supernatants. Then 0.5 $\mu$Ci[$^3$H] thymidine was added to each culture for the last 4 hr of a 24-hr incubation period. The cells were then harvested onto glass fiber filters, and radioactivity was measured in a liquid scintillation spectrometer.

2) MCGF Assay: MCGF activity was determined by a colorimetric assay (Mosmann, T. supra) with the use of MC/9 mast cells (A.T.C.C. Accession No. CRL8306). Briefly, MC/9 cells were cultured in flat-bottom Falcon microtiter trays (10$^4$ cells/well) in DME supplemented with 4% FCS, 50 $\mu$M 2-mercaptoethanol, 2 mM glutamine, non-essential amino acids, essential vitamins, and varied concentrations of test supernatants in a final volume of 0.1 ml. Fifty micrograms of 3-[4,5-dimethylthiazol-2-yl)-2,5-diphenyl tetrazolium bromide (Sigma) in 10 $\mu$l of phosphate-buffered saline were added to each cell culture after a 20-hr incubation. Four hours later, 0.1 ml of 0.04 M HCl in isopropanol was added to solubilize the colored reaction product. The absorbance at 570 nm (reference 630 nm) was measured on a Dynatek Microelisa Autoreader (MR580).

3) Ia Antigen Assay: Several DBA/2 mice (2–3 months old) were sacrificed and the spleens obtained surgically. The erythrocytes were lysed by hypotonic shock using 0.87% ammonium chloride. Then the T-cells were lysed by using cytotoxic monoclonal antibodies directed against T-cell-specific surface markers (Thy-1, Lyt-1 and Lyt-2) followed by incubation in rabbit complement. The dead cells were then removed using ficoll-hypaque density gradients. Adherent cells had been removed previously by adherence to plastic petri dishes at 37° C. At this time the cells were washed, counted and scored for viability. One million cells were incubated in 0.5 ml of tissue culture medium (RPMI 1640 or Minimal essential medium-MEM/Earle's salts) (Gibco) supplemented with 10% fetal calf serum, 2-mercaptoethanol and various antibiotics (penicillin, streptomycin and gentamicin). In experiments where the positive control consisted of supernatants from T-cells induced with the T-cell mitogen Concanavalin A, 10 mg/ml (final concentration) of alpha-methyl mannoside was added to neutralize the mitogen. After 24 hours incubation, the cells were harvested and prepared for staining with anti-I-A$^d$ monoclonal antibodies (in some experiments MK-D6 (I-A$_d$) and in some other experiments the monoclonal antibody D3.137.5.7 (anti-I-Abd) were used). These antibodies were used as first stage antibodies conjugated to either the hapten N.I.P. (MK-D6) or biotin (D3.137.5.7). The staining was then completed by incubating the cells with fluoresceinated second-stage reagents (either anti-NIP antibodies or avidin). The intensity of fluorescence staining was then determined using either a fluorescence-activated cell sorter (Becton-Dickinson, Mountain View, Calif.) or a Cytofluorograph (Ortho Diagnostics, Cambridge, Mass.).

4) Measurement of IgE and $IgG_1$ Enhancing Activity: T cell-depleted spleen cell suspensions were prepared by forcing spleen fragments through a 200-mesh wire screen. The cell suspensions were washed and incubated for 15 minutes on ice with anti-Thy-1.2. The cells were then pelleted and resuspended in 19% rabbit complement (Lo-Tox M, Cedarlane Laboratories, Hornby, Ont., Canada) diluted in RPMI-1640 containing 25 mM Hepes, pH 7.2, and 0.3% bovine serum albumin. Cells were incubated with complement for 45 minutes at 37° and the dead cells were removed by centrifugation over Ficoll (density 1.119 g/ml, Sigma, St. Louis, Mo.). All steps except the complement treatment were performed in Hanks balanced salts solution plus 0.3% bovine serum albumin.

B cells were purified by incubating spleen cell suspensions with a mixture of monoclonal antibodies to Thy-1, $L_3T_4$, Lyt-2, MAC-1, and the antibody RB6-8C5, followed by complement treatment and final centrifugation, as described above, for the removal of dead cells. The cells were then stained with fluorescein-conjugated RA3-6B2 and the cells separated into large and small positive fractions with a FACS-IV fluorescence-activated cell sorter (Becton-Dickinson, Mountain View, Calif.).

Cells were cultured in round-bottom 96-well plates (Flow Laboratories, McLean, Va.) in RPMI-1640 medium (Gibco) plus penicillin, streptomycin, glutamine, 2-mercaptoethanol ($5\times10^{-5}$ M) and 10% fetal calf serum (Hyclone, Logan, Utah). The final concentrations of cells were: B cells and T-depleted spleen cells, $5\times10^5$/ml; spleen cells, $1\times10^6$ cells/ml. Cells were cultured at twice the final cell concentration with 4 µg/ml of Salmonella typhimurium LPS (Sigma).

One day later (Cl.Lyl$^+$2$^-$/9 supernatant and/or IFN-γ were added in 0.1 ml of medium. Culture supernatants were harvested 7 days after initiation of the cultures and frozen until assayed. Balb/cByJ mice were used in all experiments except where noted. For isotype determinations, polyvinyl chloride 96-well plates (Dynatech, Alexandria, Va.) were coated for 1 hour with the appropriate first step isotype-specific antibody at con- centrations of 0.5 to 2.0 µg/ml. These plates were blocked with phosphate-buffered saline plus 0.1% bovine serum albumin and 0.04% Tween 20. Standard curve solutions and supernatants to be tested were added in 0.1 ml, all dilutions being made in RPMI-1640 plus 5% fetal calf serum. After three hours at room temperature, the plates were washed in phosphate-buffered saline plus 0.04% Tween 20 and the appropriate NIP or biotin conjugated second step antibody at concentrations of 0.25 to 2.0 µg/ml. After incubation for 1 hour at room temperature, these plates were washed as before an an optimum concentration of either horseradish peroxidase conjugated monoclonal anti-NIP or horseradish peroxidase conjugated avidin (Vector Laboratories, Burlingame, Calif.) was added. One hour later, the plates were washed and 0.1 ml was added of a substrate solution containing 1 mg/ml 2,2'-azinobis(3-ethylbenzthiazolinesulfonic acid) (Sigma) and 0.003% $H_2O_2$ in 0.1 M $Na_2HPO_4$ and 0.05 M citric acid. The reaction was stopped by the addition of 0.05 ml of 0.2 M citric acid and the plates read on a Dynatech ELISA reader. For the IgE ELISA, plates were coated with a monoclonal anti-IgE, EM95, and the second step was NIP-conjugated purified rabbit anti-IgE antibody. IgM, $IgG_{2a}$, $IgG_{2b}$, $IgG_3$, and IgA ELISA used the same isotype-specific rabbit antibodies as a first step and as a NIP-conjugated second step. $IgG_1$ was assayed using unconjugated and biotin-conjugated preparations of the same $IgG_1$-specific rabbit antibodies.

Specificity of each isotype-specific ELISA was tested by assaying 20 µg/ml solutions of two or more purified monoclonal immunoglobulins of each of the other 6 isotypes under the same conditions used for the appropriate isotype. In all cases, the 20 µg/ml solution gave a reading no higher than the lowest concentration on the standard curve (ranging from 1.25 ng/ml for IgE to 3.1 ng/ml for IgM). Further evidence of specificity can be deduced from the independent variation of isotypes under different culture conditions.

C. Isolation of mRNA from T Cells

1) Total cellular DNA was isolated from cells using the guanidine isothiocyanate procedure of Chirgwin, J. et al., (Biochemistry, 18: 5294–5299 [1979]).

Frozen cell pellets from ConA-induced helper cells (12 hrs after stimulation) were suspended in guanidine isothiocyanate lysis solution. Twenty ml of lysis solution was used for $1.5\times10^8$ cells. Pellets were resuspended by pipetting, then DNA was sheared by 4 passes through a syringe using a 16 gauge needle. The lysate was layered on top of 20 ml of 5.7 M CsCl, 10 mM EDTA in 40 ml polyallomer centrifuge tube. This solution was centrifuged at 25,000 rpm in a Beckman SW28 rotor (Beckman Instruments, Inc., Palo Alto, Calif.) for 40 hrs at 15° C. The guanidine isothiocyanate phase containing DNA was pipetted off from the top, down to the interface. The walls of the tube and interface were washed with 2–3 ml of guanidine isothiocyanate lysis solution. The tube was cut below the interface with scissors, and the CsCl solution was decanted. RNA pellets were washed twice with cold 70% ethanol. Pellets were then resuspended in 500 µl of 10 mM Tris.HCl pH 7.4, 1 mM EDTA, 0.05% SDS. 50 µl of 3M sodium acetate was added and RNA was precipitated with 1 ml ethanol. About 0.3 mg total RNA was collected by centrifuging and the pellets washed once with cold ethanol.

2) PolyA$^+$ mRNA isolation:

Washed and dried total RNA pellet was resuspended in 900 µl of oligo (dT) elution buffer (10 mM Tris.HCl, pH 7.4, 1 mM EDTA, 0.5% SDS). RNA was heated for 3 min. at 68° C. and then chilled on ice. 100 µl of 5 M NaCl was added. The RNA sample was loaded onto a 1.0 ml oligo (dT) cellulose column (Type 3, Collaborative Research, Waltham, Mass.) equilibrated with binding buffer (10 mM Tris.HCl pH 7.4, 1 mM EDTA, 0.5 M NaCl, 0.5% SDS.). Flow-through from the column was passed over the column twice more. The column was then washed with 20 ml binding buffer. PolyA$^+$ mRNA was collected by washing with elution buffer. RNA usually eluted in the first 2 ml of elution buffer. RNA was precipitated with 0.1 volume 3 M sodium acetate (pH 6) and two volumes of ethanol. The RNA pellet was collected by centrifugation, washed twice with cold ethanol, and dried. The pellet was then resuspended in water. Aliquots were diluted, and absorbance at 260 nm was determined.

D. cDNA Library Construction

1) Preparation of vector primer and oligo dG-tailed linker DNAs:

The procedure of Okayama & Berg (Mol. & Cell. Biol. 2:161–170 [1982]) was used with only minor modifications and adapted to the pcDV1 and pL1 plasmids described by Okayama & Berg (Mol. & Cell. Biol. 3:380–389 [1983]). Specifically, a modified pcDV1 plasmid containing an NsiI site at the previous location of the KpnI site.

An 80 µg sample of pcDV1 DNA was digested at 30° C. with 20 U of KpnI endonuclease in a reaction mixture of 450 µl containing 6 mM Tris.HCl (pH 7.5), 6 mM $MgCl_2$, 6 mM NaCl, 6 mM 2-ME, and 0.1 mg of bovine serum albumin (BSA) per ml. After 16 hr the digestion was terminated with 40 μl of 0.25 M EDTA (pH 8.0) and 20 μl of 10% sodium dodecyl sulfate (SDS); the DNA was recovered after extraction with water-saturated 1:1 phenol-CHCl₃ (hereafter referred to as phenol-CHCl₃) and ethanol precipitation. Homopolymer tails averaging 60, but not more than 80, deoxythymidylate (dT) residues per end were added to the NsiI endonuclease-generated termini with calf thymus terminal transferase as follows: The reaction mixture (38 μl) contained sodium cacodylate-30 mM Tris.HCl pH 6.8 as buffer, with 1 mM CoCl₂, 0.1 mM dithiothreitol, 0.25 mM dTTP, the NsiI endonuclease-digested DNA, and 68 U of the terminal deoxynucleotidyl transferase (P-L Biochemicals, Inc., Milwaukee, Wis.). After 30 min. at 37° C. the reaction was stopped with 20 μl of 0.25 M EDTA (pH 8.0) and 10 μl of 10% SDS, and the DNA was recovered after several extractions with phenol-CHCl₃ by ethanol precipitation. The DNA was then digested with 15 U of EcoRI endonuclease in 50 μl containing 10 mM Tris.HCl pH 7.4, 10 mM MgCl₂, 1 mM dithiothreitol, and 0.1 mg of BSA per ml for 5 hr at 37° C. The large fragment, containing the SV40 polyadenylation site and the pBR322 origin of replication and ampicillin-resistance gene, was purified by agarose (1%) gel electrophoresis and recovered from the gel by a modification of the glass powder method (Vogelstein, B. & Gillespie, D., Proc. Nat. Acad. Sci. 76: 615–619 [1979]). The dT-tailed DNA was further purified by absorption and elution from an oligo (dA)-cellulose column as follows: The DNA was dissolved in 1 ml of 10 mM Tris.HCl pH 7.3 buffer containing 1 mM EDTA and 1 M NaCl, cooled at 0° C., and applied to an oligo (dA)-cellulose column (0.6 by 2.5 cm) equilibrated with the same buffer at 0° C. and eluted with water at room temperature. The eluted DNA was precipitated with ethanol an dissolved in 10 mM Tris.HCl pH 7.3 with 1 mM EDTA.

The oligo (dG) tailed linker DNA was prepared by digesting 75 μg of pL1 DNA with 20 U of PstI endonuclease in 450 μl containing 6 mM Tris.HCl pH 7.4, 6 mM MgCl₂, 6 mM 2-ME, 50 mM NaCl, and 0.01 mg of BSA per ml. After 16 hr at 30° C. the reaction mixture was extracted with phenol-CHCl₃ and the DNA was precipitated with alcohol. Tails of 10 to 15 deoxyguanylate (dG) residues were then added per end with 46 U of terminal deoxynucleotidyl transferase in the same reaction mixture (38 μl) as described above, except that 0.1 mM dGTP replaced dTTP. After 20 min. at 37° C. the mixture was extracted with phenol-CHCl₃, and after the DNA was precipitated with ethanol it was digested with 35 U of HindIII endonuclease in 50 μl containing 20 mM Tris.HCl pH 7.4, 7 mM MgCl₂, 60 mM NaCl, and 0.1 mg of BSA at 37° C. for 4 hr. The small oligo (dG)-tailed linker DNA was purified by agarose gel (1.8%) electrophoresis and recovered as described above.

2) cDNA Library Preparation:

Step 1: cDNA synthesis. The reaction mixture (10 μl) contained 50 mM Tris.HCl pH 8.3, 8 mM MgCl₂, 30 mM KCl, 0.3 mM dithiothreitol, 2 mM each dATP, dTTP, dGTP, and dCTP, 20 μCi $^{32}$p-dCTP (3000 Ci/mmole), 3 μg polyA⁺ RNA from Con-A induced T-cells, 60 units TNasin (Biotec, Inc., Madison, Wis.), and 2 μg of the vector-primer DNA (15 pmol of primer end), and 45 U of reverse transcriptase. The reaction was incubated 60 min at 42° C. and then stopped by the addition of 1 μl of 0.25 M ETDA (pH 8.0) and 0.5 μl of 10% SDS; 40 μl of phenol-CHCl₃ was added, and the solution was blended vigorously in a Vortex mixer and then centrifuged. After adding 40 μl of 4 M ammonium acetate and 160 μl of ethanol to the aqueous phase, the solution was chilled with dry ice for 15 min., warmed to room temperature with gentle shaking to dissolve unreacted deoxynucleoside triphosphates that had precipitated during chilling, and centrifuged for 10 min. in an Eppendorf microfuge. The pellet was dissolved in 10 μl of 10 mM Tris.HCl pH 7.3 and 1 mM EDTA, mixed with 10 μl of 4 M ammonium acetate, and reprecipitated with 40 μl of ethanol, a procedure which removes more than 99% of unreacted deoxynucleotide triphosphates. The pellet was rinsed with ethanol.

Step 2: Oligodeoxycytidylate [oligo (dC)] addition. The pellet containing the plasmid-cDNA:mRNA was dissolved in 20 μl of 140 mM sodium cacodylate-30 mM Tris.HCl pH 6.8 buffer containing 1 mM CoCl₂, 0.1 mM dithiothreitol, 0.2 μg of poly (A), 70 μM dCTP, 5 μCi $^{32}$p-dCTP, 3000 Ci/mmole, and 60 U of terminal deoxynucleotidyl transferase. The reaction was carried out at 37° C. for 5 min. to permit the addition of 10 to 15 residues of dCMP per end and then terminated with 2 μl of 0.25 M EDTA (pH 8.0) and 1 μl of 10% SDS. After extraction with 20 pl of phenol-CHCl₃, the aqueous phase was mixed with 20 μl of 4 M ammonium acetate, the DNA was precipitated and reprecipitated with 80 μl of ethanol, and the final pellet was rinsed with ethanol.

Step 3: HindIII endonuclease digestion. The pellet was dissolved in 30 μl of buffer containing 20 mM Tris.HCl pH 7.4, 7 mM MgCl₂, 60 mM NaCl, and 0.1 mg of BSA per ml and then digested with 10 U of HindIII endonuclease for 2 hr at 37° C. The reaction was terminated with 3 μl of 0.25 M EDTA (pH 8.0) and 1.5 μl of 10% SDS and, after extraction with phenol-CHCl3 followed by the addition of 30 μl of 4 M ammonium acetate, the DNA was precipitated with 120 μl of ethanol. The pellet was rinsed with ethanol and then dissolved in 10 μl of 10 mM Tris.HCl (pH 7.3) and 1 mM EDTA, and 3 μl of ethanol was added to prevent freezing during storage at –20° C.

Step 4: Cyclization mediated by the oligo (dG)-tailed linker DNA. A 9 μl sample of the HindIII endonuclease-digested oligo (dC)-tailed cDNA;mRNA plasmid (about 90% of the sample) was incubated in a mixture (90 μl) containing 10 mM Tris.HCl pH 7.5, 1 mM EDTA, 0.1 M NaCl, and 1.8 pmol of the oligo (dG)-tailed linker DNA at 65° C. for 5 min., shifted to 42° C. for 60 min, and then cooled to 0° C. The mixture (90 μl) was adjusted to a volume of 900 μl containing 20 mM Tris.HCl pH 7.5, 4 mM MgCl₂, 10 mM (NH₄)₂SO₄, 0.1 M KCl, 50 μg of BSA per ml, and 0.1 mM β-NAD; 6 μg of E. coli DNA ligase were added and the solution was then incubated overnight at 12° C.

Step 5: Replacement of RNA strand by DNA. To replace the RNA strand of the insert, the ligation mixture was adjusted to contain 40 μM of each of the four deoxynucleoside triphosphates, 0.15 mM b-NAD, 4 μg of additional E. coli DNA ligase, 16 U of E. coli DNA polymerase I (PolI,) and 9 U of E. coli RNase H. This mixture (960 μl) was incubated successively at 12° C. at room temperature for 1 hr to promote optimal repair synthesis and nick translation by PolI.

Step 6: Transformation of E. coli. Transformation was carried out using minor modifications of the procedure described by Cohen et al. (Proc. Nat. Acad. Sci. U.S.A., 69:2110–2114 [1972]). E. coli K-12 strain MC1061 (Casadaban, M. and Cohen, S., J. Mol. Biol. 138:179–207 [1980]) was grown to 0.5 absorbancy unit at 600 nm at 37° C. in 300 ml of L-broth. The cells were collected by centrifugation, suspended in 30 ml of 10 mM Pipes. pH 7, 60 mM CaCl₂, 15% glycerol and centrifuged at 0° C. for 5 min. The cells were resuspended in 24 ml of the above buffer and incubated again 0° C. for 5 min.; then, 1.0 ml aliquots of the cell suspensions were mixed with 0.1 ml of the DNA solution (step 5) and incubated at 0° C. for 20 min. Next the cells were kept at 42° C. for 2 min. and thereafter at room temperature for 10 min.; then 1 liter of L-broth was added, and the culture was incubated at 37° C. for 60 min. Ampicillin was added to a concentration of 50 μg/ml. The culture was shaken for an additional 10 hrs. at 37° C. Dilutions of this culture were spread on L-broth agar containing 50 μg/ml ampicillin. After incubation at 37° C. for 12 to 24 hr, individual colonies were picked with sterile tooth-picks. In all, approximately $1 \times 10^5$ independent cDNA clones were generated.

E. Screening of the T-cell cDNA Library by DNA Transfections $10^4$ single clones were picked at random from the T-cell cDNA library and propagated individually in wells of microtiter dishes containing 200 μl L-broth with ampicillin at 50 μg/ml and dimethyl sulfoxide at 7%. To focus only on the novel MCGF activity, 53 IL-3 cDNA clones and one GM-CSF cDNA clone identified by hybridization with the appropriate $^{32}$P-labelled cDNA probes were eliminated as follows: Each plate of 96 cultures was replicated onto nitrocellulose filters for hybridization screening. Hybridizations were performed in 6×SSPE (1×SSPE=180 mM NaCl; 10 mM sodium phosphate, pH 7.4; 1 mm EDTA), 0.1% SDS, 100 μg/ml E. coli tRNA, 50% formamide, for 16 hrs. at 42° C. Hybridizing clones were identified by autoradiography of the washed filters. These clones were removed by sterilizing the microtiter wells containing these clones with ethanol prior to the preparation of clone pools. Pools containing up to 48 cDNA clones were prepared from the microtiter cultures. Two hundred such pools were grown up in 1 liter cultures of L-broth containing 100 μg/ml ampicillin. Plasmid DNA was isolated from each culture and purified by twice banding through CsCl gradients. The DNA representing each pool was transfected into COS monkey cells as follows.

One day prior to transfection, approximately $10^6$ COS monkey cells were seeded onto individual 100 mm plates in DME containing 10% fetal calf serum and 2 mM glutamine. To perform the transfection, the medium was aspirated from each plate and replaced with 4 ml of DME containing 50 mM Tris.HCl pH 7.4, 400 μg/ml DEAE-Dextran and 50 μg of the plasmid DNAs to be tested. The plates were incubated for four hours at 37° C., then the DNA-containing medium was removed, and the plates were washed twice with 5 ml of serum-free DME. DME containing 150 μM chloroquine was added back to the plates which were then incubated for an additional 3 hrs at 37° C. The plates were washed once with DME and then DME containing 4% fetal calf serum, 2 mM glutamine, penicillin and streptomycin was added. The cells were then incubated for 72 hrs at 37° C. The growth medium was collected and evaluated in the various bioassays.

An initial set of plasmid pools was screened primarily by using proliferation assays with the HT-2 and MC/9 cell lines. Among the first 110 pools assayed on these two cell lines, eight produced significant activity in the HT-2 assay. Several of these pools had weak but significant MCGF activity, but because the MCGF activities were generally weaker and more variable, we did not rely on this assay for identifying positive pools.

Approximately half of the COS supernatants from the random pool transfections were also assayed for Ia inducing activity on mouse B cells. Among the pools tested, each pool shown to be active for TCGF activity was found also to have Ia inducing activity. Thus, there was a perfect correlation between the TCGF activity and the Ia inducing activity.

F. Isolation of Functional Mouse cDNA Clones that Express TCGF and MCGF Activities One pool, 2A, which was reproducibly the most active in all assays, was subdivided into smaller subpools representing horizontal and vertical rows of the 48 well microtiter plate. One horizontal and one vertical subpool were positive for both MCGF and TCGF activities. The single clone, 2A-E3, common to both subpools was then grown individually and its plasmid DNA was transfected as before. The resulting COS supernatant was then assayed for the presence of various activities, including colony formation, MCGF, TCGF, Ia inducing, and IgE and IgG, enhancing activities.

A 366 base-pair-long PstI fragment isolated from clone 2A-E3 (FIG. 1A) and labelled with $^{32}$P was used as a probe to screen pools which had been positive for biological activity as well as other untested pools. The screening was performed by hybridization to filters replicated with the microtiter cultures as described above. Nine hybridizing clones were isolated and their DNA analyzed by restriction mapping. All pools which exhibited biological activity contained at least one hybridizing clone which shared a common restriction cleavage map with clone 2A-E3. The frequency of hybridizing clones among the $10^4$ which were picked suggests a frequency of approximately 0.2% in the total library. Of the hybridizing clones which were tested, approximately 90% expressed a functional protein.

G. Some Biological Activities of Clone 2A-E3

Figure 3B:
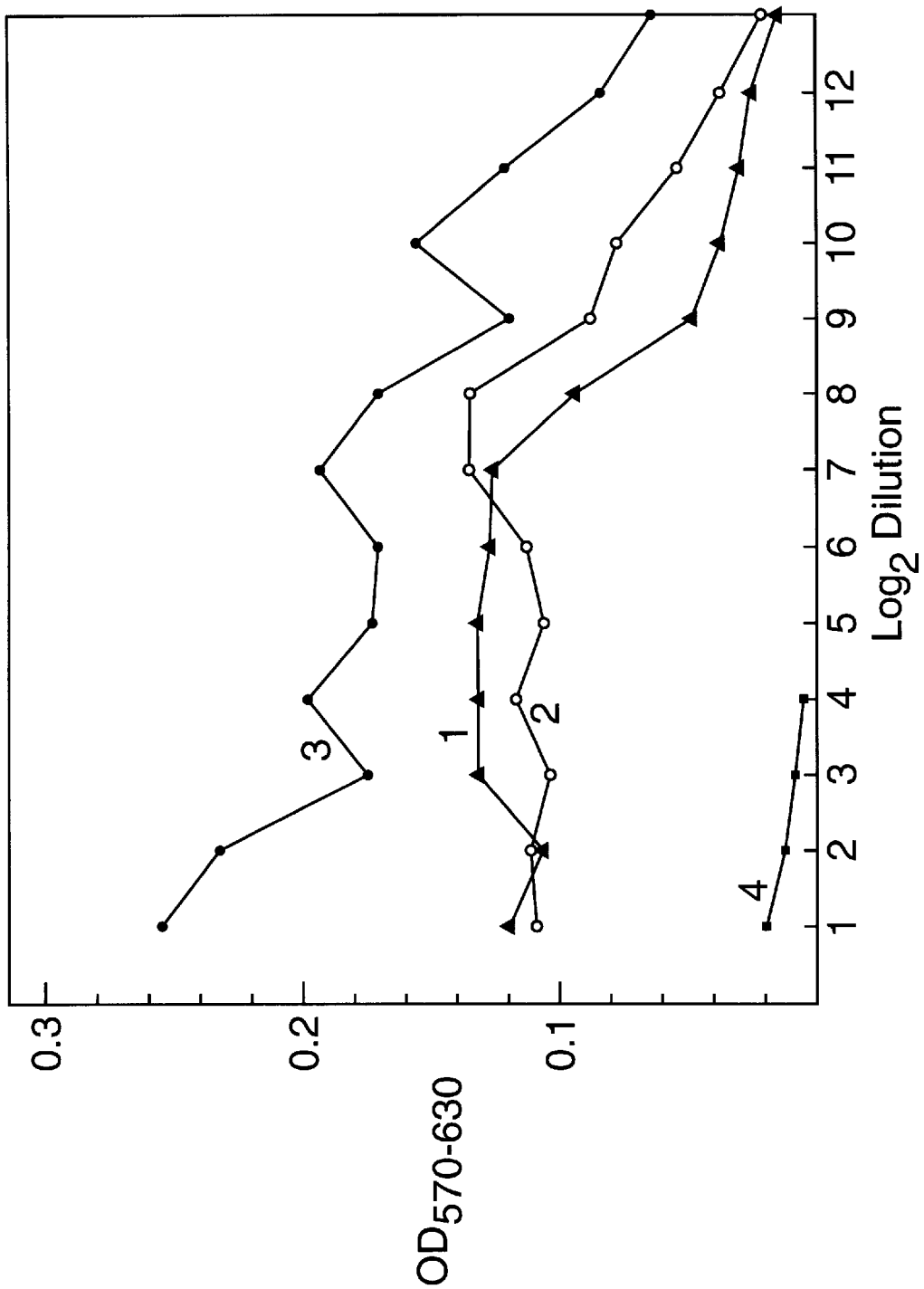
FIGS. 3A, 3B & 3C illustrate some of the biological activities of supernatant from COS cells transfected with a cDNA clone of the present invention. (A) TCGF activity was determined with HT-2 cells using a colorimetric assay. Samples: 1) 2A-E3 COS supernatant. 2) Cl.Lyl$^+$2$^-$/9 cell supernatant. 3) COS-IL-2. 4) Mock transfected COS supernatant. (B) MCGF activity was determined using MC/9 mast cells and a colorimetric assay. Samples: 1) 2A-E3 COS supernatant. 2) COS-IL-3. 3) Cl.Lyl$^+$2$^-$/9 supernatant. 4) Mock transfected COS supernatant. (C) Expression of Ia antigen on B-cells cultured in test samples was determined by fluorescent staining. 1) 2A-E3 COS supernatant. 2) Cl.Lyl$^+$2$^-$/9 cell supernatant. 3) Mock transfected COS supernatant. The fluorescence units were calculated by multiplying the percentage of positive cells in each sample by the intensity of fluorescent staining. (D) IgE (left) and IgG$_1$ (right) levels in supernatants of LPS stimulated B-cells cultured with test samples are shown. 1) Medium only. 2) 20% COS mock. 3) 20% Cl.Lyl$^+$2$^-$/9 plus 20% COS mock supernatant. 4) 20% 2A-E3 COS supernatant. Specific immunoglobulin production was determined using an isotype specific ELISA assay.

When supernatant from COS cells transfected with the single 2A-E3 clone is tested for TCGF activity on HT-2 cells, the dose response curve reaches the same maximum level as seen with supernatant from Cl.Lyl$^+$2$^-$/9 cells (FIG. 3A). Even at saturating levels, however, the COS supernatant does not achieve the same level of stimulation obtained with recombinant IL-2. When the same COS supernatant is tested on MC/9 mast cells, the maximal stimulation is approximately the same as with recombinant IL-3 (FIG. 3B). These results, employing a colorimetric assay (Mosmann, T., supra), were also confirmed using incorporation of [$^3$H] thymidine.

The COS-expressed material of clone 2A-E3 was also tested for two activities of BSF-1, induction of Ia expression on mouse B cells (Noelle, R. et al., Proc. Natl. Acad. Sci. U.S.A. 81:6149–6153 [1984] and Roehm, N. et al., J. Exp. Med. 169:679–694 [1984]; both of which are incorporated herein by reference) and enhancement of IgG$_1$ and IgE production as described above.

Figure 3D:
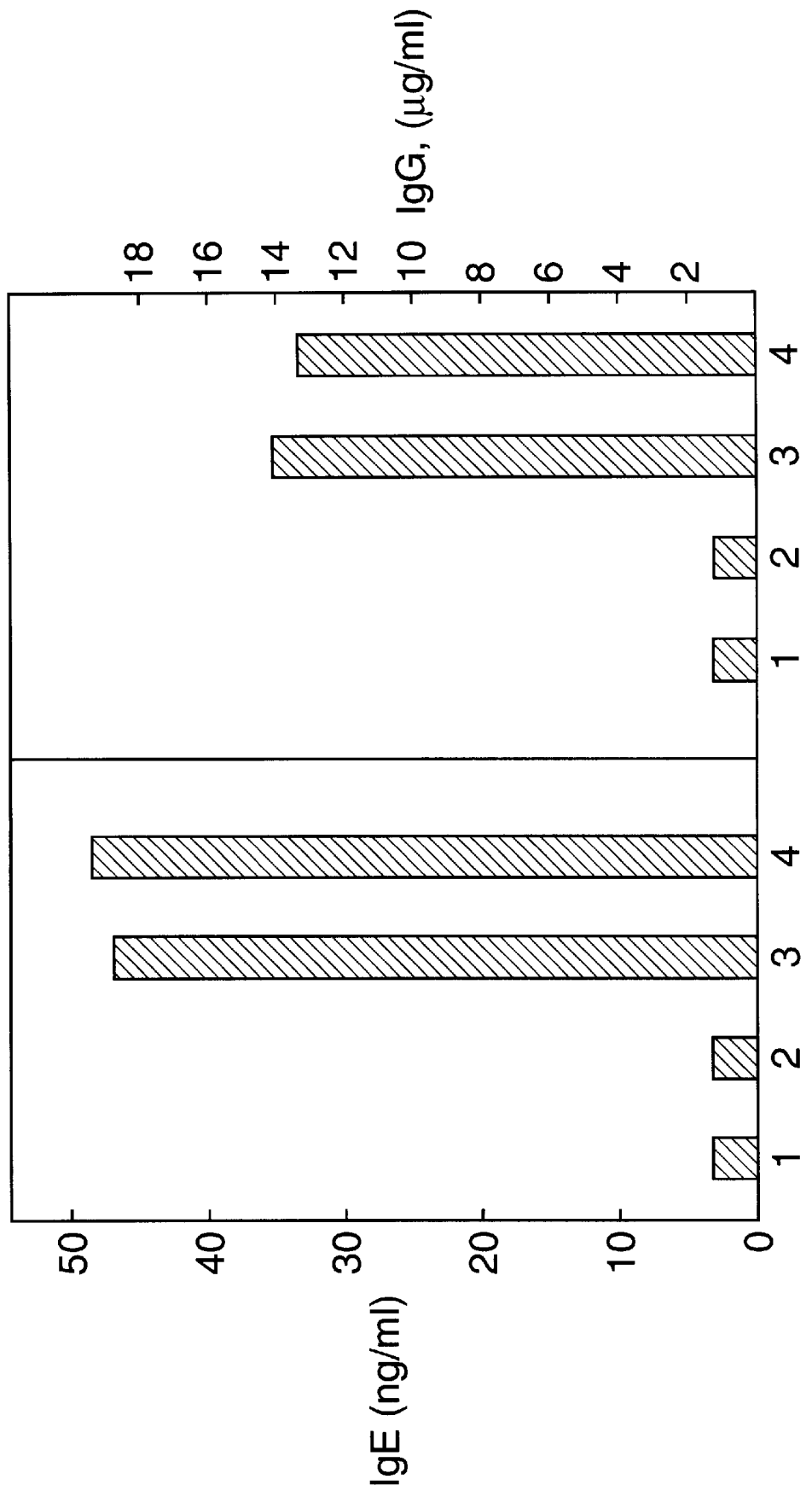

The COS supernatant had significant Ia inducing activity (FIG. 3C), and enhanced the secretion of both IgE and IgG$_1$, by LPS stimulated B cells (FIG. 3D). Results with this cDNA clone clearly show that all these activities are associated with a single gene product. An assay for stimulation of fibroblast growth using mouse 3T3 cells was negative.

H. Structure of the cDNA Insert for Clone 2A-E3

Figure 2B:
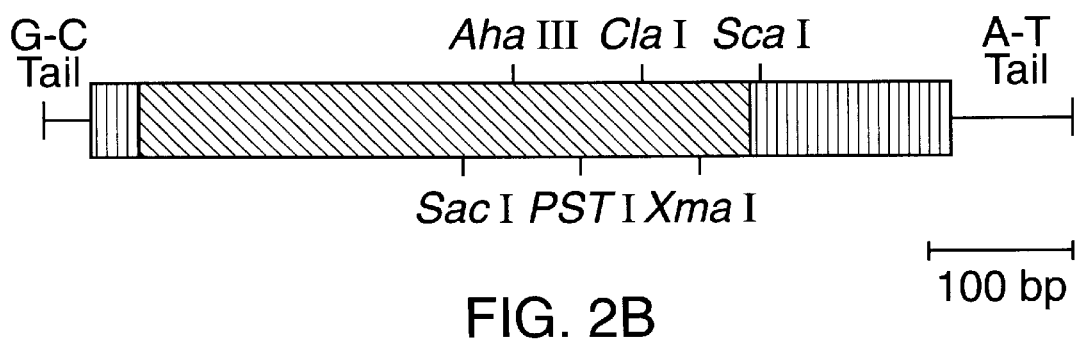

The cDNA insert was initially analyzed by restriction endonuclease digestion; a restriction cleavage map of the cDNA insert and the structure of the plasmid vector are shown in FIG. 2. The DNA sequence of the entire cDNA insert (FIG. A) was then determined using a standard combination of Maxam-Gilbert chemical cleavage and dideoxy chain termination methods well known to those in the art. The cDNA insert is 585 base pairs long excluding the poly A tail. There is a single long open reading frame, with the first ATG codon located 56 nucleotides from the 5' end followed by 140 codons ending with the termination codon TAG at nucleotide positions 476–478. The NH2-terminal segment of the predicted polypeptide is hydrophobic, as would be expected for a secreted protein.

I. Expression of the Native Protein in T Cells and Homology to Mouse IL-2 and IL-3

Assays of cell supernatants indicated that the expression of this gene product is inducible by Con A in Cl.Lyl$^+$2$^-$/9 cells. Inducible expression of this gene was confirmed by analysis of mRNA isolated from cells treated or untreated with Con A, which analysis indicated that a single prominent mRNA species was detected only in mRNA isolated from induced T-cells. mRNA samples from several mouse cell lines were then analyzed with the same radiolabelled probe. Hybridization was detected in mRNA from the EL-4 cell line treated with the phorbol ester, PMA. EL-4 is known to produce BSF-1 under these conditions. Two other lines tested GK15-1 and LB2-1, represent a subset of T-cells which do not produce combined MCGF/TCGF activities, and no hybridization with the labelled probe was observed with the GK15-1 or LB2-1 mRNA samples. These results show that there is good correlation between production of biological activities and expression of the mRNA.

Despite the biological activities of the polypeptides of the present invention that are similar to activities of IL-2 and IL-3, there is no significant nucleotide sequence homology between the mouse cDNA clones of this invention and either mouse IL-2 or IL-3 cDNA sequences. At the amino acid sequence level, however, there are two regions which can be discerned to have homology with these two gene products. Amino acid residues 32–39 are 70% homologous to residues 49–56 of the IL-3 precursor polypeptide (Yokota, T. et al., Proc. Natl. Acad. Sci. U.S.A. 81:1070–1074 [1984]). Amino acids 95–103 are 60% homologous with residues 52–61 of mouse IL-2 (Yokota, T. et al., Proc. Natl. Acad. Sci. U.S.A. 82:68–72 [1985]). There are no other homologies which could be detected with other cloned lymphokines, such as gamma interferon (IFN) or interleukin-1.

Both the biological activity data and analysis of mRNA levels suggest that Cl.Lyl$^+$2$^-$/9 cells produce high levels of this interleukin. Analysis of various T-cell clones suggests that only certain T-cells express this gene product, and this subset often does not synthesize IL-2 or gamma interferon.

Example II

This example demonstrates the isolation of two cDNA clones containing genes encoding polypeptides of the present invention that are active, in particular, on human cells.

A. Human Cells

1) Human T Cell Line (2F1) and Peripheral Blood Lymphocytes (PBL)

A human helper T-cell clone, 2F1, and human peripheral blood lymphocytes (PBL's) were grown in Iscove's medium supplemented with 3% fetal calf serum. The 2F1 cells were activated with Con A (10 ug/ml) and PBL's were stimulated with 1 ng/ml PNA for 12 h, after which Con A at 5 ug/ml was added. The cells were harvested 4 hr (2F1) or 10 hr (PBL's) after addition of Con A.

2) Cell Suspensions a) Preparation of human B cells

Enriched B cell preparations were isolated from human tonsils which were obtained at tonsillectomy from patients with chronic tonsillitis. Tonsil cells were dispersed into single cell suspensions. The mononuclear cells were isolated by Ficoll-Hypaque density gradient centrifugation (Pharmacia, Uppsala, Sweden) following the technique of Boyum, I. (1968) Scand. J. Clin. Lab. Invert. 21 (Suppl. 97) 77). B cells were recovered after elimination of T-cells by rosetting with A.E.T. (2 aminoethylisothiouronium bromide) treated sheep red blood cells. The rosetted cell mixture was layered over Ficoll Hypaque, and the rosette forming cells were separated from the non-rosette forming cells by centrifugation (20 min at 800 g).

After centrifugation, B cells were recovered at the interface and the contaminating T-lymphocytes (5%) were further removed by a second cycle of resetting. The B cell preparations contained >95% sIg$^+$ cells as determined by staining with a fluorescein conjugated F(ab')2 fragment goat anti-human Ig; >95% human B cell specific antigen positive cells as determined by staining cells with a mouse anti-human B cell specific monoclonal antibody: B1 (Coulter, Hialeh, Fla.) and fluorescein conjugated F(ab')2 goat anti-mouse lg (Grub, Wien, Austria). The contamination with T-cells was less than 1% as determined by the monoclonal antibody Leu-1 (Becton Dickinson, Mountain View, Calif.) or the monoclonal antibody OKT11 (Ortho, Raritan, N.J.). For activation, the B lymphocytes are resuspended in Yssel's culture medium (Yssel, H. et al. J. Immunological Methods 72:219(1984)) at 5×10$^5$ per ml in a volume of 3 ml per well of a 6-well tissue culture plate (Falcon, Ref. 3046, Oxnard, Calif.). The B-cells were cultured at 37° C. and in an atmosphere containing 5% $CO_2$.

b) Activation of human B cells

Two different activators were used:

i) *Staphylococcus aureus* strain Cowan I (SAC): SAC is obtained as Pansorbin (Calbiochem, La Jolla, Calif.). It is added to the B cell cultures at a final concentration of 0.01%. Cells were activated by cultivation at 37° C. and 5% $CO_2$ for 24 hours, and were subsequently centrifuged over Ficoll Hypaque in order to remove non-viable cells and the SAC particles.

ii) Anti IgM antibodies coupled to beads (Biorad, Richmond, Calif.): The beads are added at a final concentration of 5 ug anti IgM antibody per ml of culture. Cells are activated by cultivation at 37° C. and 5% $CO_2$ for 72 hours and subsequently isolated by centrifugation over Ficoll Hypaque to remove the beads and the non-viable cells.

c) A human T-cell clone, JL-EBV, was stimulated with irradiated (4500R) cells of a human EBV-transformed B-cell line, and subsequently maintained in RPMI 1640 medium containing 10% human AB serum, 50 uM 2-mercaptoethanol and recombinant human IL-2. Five to ten days after stimulation, JL-EBV cells were used as targets in a two-day TCGF assay, using the colorimetric MTT method described previously.

3) Proliferation assays a) Assay of BCGF activity

Cell proliferation was measured by $^3$H-thymidine incorporation. The activated low density B cells are washed twice with culture medium and resuspended at 10$^6$ per ml. 5×10$^4$ B lymphocytes in 50 ul medium were dispensed into 96 well, flat bottomed microtiter trays (Falcon, Ref 3072). 50 ul of supernatants to assay were added appropriately diluted. All assays were carried out in triplicate. After two days (anti p cultures), or three days (SAC cultures), the microcultures were pulsed with 1 $\mu$Ci tritiated thymidine (25 MCi/mmole, CEA, Saclay, France) per well and were harvested 15 hours later using a MASH (Microbiological Associates, Bethesda, Md.). Dried glassfiber filters were counted in an LKB scintillation counter (LKB, Bromma, Sweden) after transfer into vials containing scintillation fluid (Ready Solv EP, Beckman, Fullerton, Calif.).

The B-cell growth factor activity of the tranfection supernatants was compared to that of the following reagents: recombinant IL-2, commercial BCGF purified from peripheral blood cell culture supernatants stimulated with PHA (Cytokine Technology International, Buffalo, N.Y.), recombinant human gamma IFN, supernatant from a ConA stimulated human T-cell clone containing BCGF activity (HG 120).

b) Assay of TCGF activity

The human helper T-cell clone JL-EBV was stimulated with irradiated (4500R) cells of a human EBV-transformed B-cell line, and subsequently maintained in RPMI 1640 medium containing 10% human AB serum, 50 uM 2-mercaptoethanol (2ME) and recombinant human IL-2. Human PBL's were stimulated with PHA (20 ug/ml) and maintained in RPMI 1640 containing 10% FBS, 50 uM 2ME and recombinant human IL-2. Five to ten days after stimulation, JL-EBV cells or PHA blasts were used as targets in a two-day TCGF assay, using the colorimetric MTT method described previously or in a three-day TCGF assay, using [$^3$H]thymidine incorporation.

B. mRNA Isolation: pcD Library Construction; and DNA Hybridizations; and DNA Transfections All of the procedures were carried out essentially as described in Example I above.

pcD cDNA libraries were constructed with mRNA from ConA-induced 2F1 cells and peripheral blood lymphocytes by using a modified pcDV1 plasmid containing an NsiI site at the previous location of the KpnI site (Lee, F. et al. Proc. Natl. Acad. Sci. U.S.A. 82:4360–4364[1985]), which is incorporated herein by reference. Each of the DNA libraries contained a minimum of $5 \times 10^5$ independent clones.

A PstI fragment was isolated from a mouse 2A-E3 cDNA clone, labeled by nick translation ($1 \times 10^8$ cpm/μg) and used to probe nitrocellulose filters containing plasmid DNA preparations from ten pools, each representing approximately $1 \times 10^3$ clones of 2F1 cDNA library. Low stringency hybridization conditions (overnight at 42° C.) were used: 6×SSPE (1×SSPE=180 mM NaCl/10 mM sodium phosphate, pH 7.4/ 1 mM EDTA) (Maniatis, T. et al. "Molecular Cloning: A Laboratory Manual", Cold Spring Harbor Laboratory, New York [1982]), 20% (vol/vol) formamide, 0.1% sodium dodecyl sulfate, yeast carrier tRNA at 100 μl. The filters were washed with 2×SSPE, 0.1% sodium dodecyl sulfate at 37° C.

C. Identification and Analysis of Hybridizing Human cDNA Clones

This positive pool was used in further colony filter hybridizations to identify a single clone that hybridized with the mouse probe (clone #46).

After making a restriction endonuclease cleavage map of clone #46, two human peripheral blood lymphocyte pcD libraries were screened, using an NheI-EcoRI fragment as probe, under stringent conditions. Five cDNA clones were identified out of $1 \times 10^5$ clones screened in one library and one cDNA clone out of $1 \times 10^4$ clones from the second. Analysis with restriction endonucleases showed that each of the hybridizing clones is identical in structure to the 2F1-derived cDNA clone #46 (pcD-46).

The DNA sequence of the cDNA insert of clone #46 was determined and is shown in FIG. 1B. The cDNA insert is 615 bp long, excluding the poly(A) tail. There is a single open reading frame, with the first ATG codon located at 64 nucleotides from the 5' end followed by 153 codons ending with the termination codon TAG at nucleotide positions 523–525. The NH2-terminal segment of the predicted polypeptide is hydrophobic, as would be expected for a secreted protein.

A comparison between the coding regions of a human and a mouse cDNA of the present invention revealed that the regions of the human cDNA coding sequence in pcD-46 covered by amino acid positions 1–90 and 129–149 share approximately 50% homology with the corresponding regions of the mouse cDNA (2A-E3) coding sequence. These regions, and 5' and 3' untranslated regions, share about 70% homology between the two cDNA sequences from the different species, whereas the region covered by amino acids 91–128 of the human protein shares very limited homology with the corresponding mouse region. In all, six of the seven cysteine residues in the human protein are conserved in the related mouse protein. Some amino acid sequence homology exists between a native form of a human polypeptide of the present invention and mouse IL-3. Amino acid residues 7–16 and 120–127 are 50% and 55% homologous, respectively, to residues 16–27 and 41–49 of the mouse IL-3 precursor polypeptide (Yokota, T. et al., Proc. Natl. Acad. Sci. U.S.A. 81:1070–1074 [1984]).

D. Some Biological Activities of Polypeptides Encoded by Human cDNA Clones

Figure 4A:
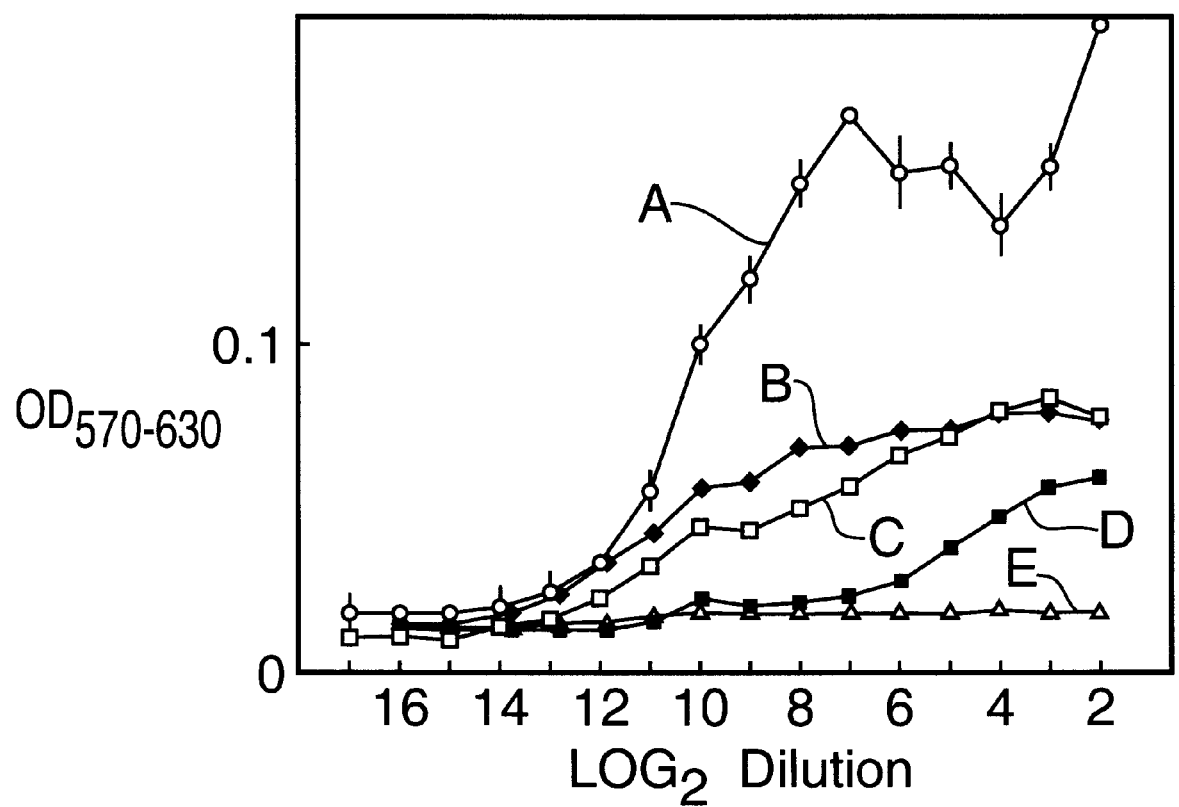
FIG. 4 illustrates some of the biological activities of supernatants from COS or L cells transfected with other cDNA clones of the present invention (isolates from a human cDNA library). (A) TCGF activity was determined with JL-EBV cells using a colorimetric (MTT) assay. (B) TCGF activity was also determined with PBL-PHA T-cell blasts using a colorimetric assay. (C) TCGF activity was further analyzed on PBL-PHA T-cell blasts using a [$^3$H]-thymidine incorporation assay. Samples.
Figure 4B:
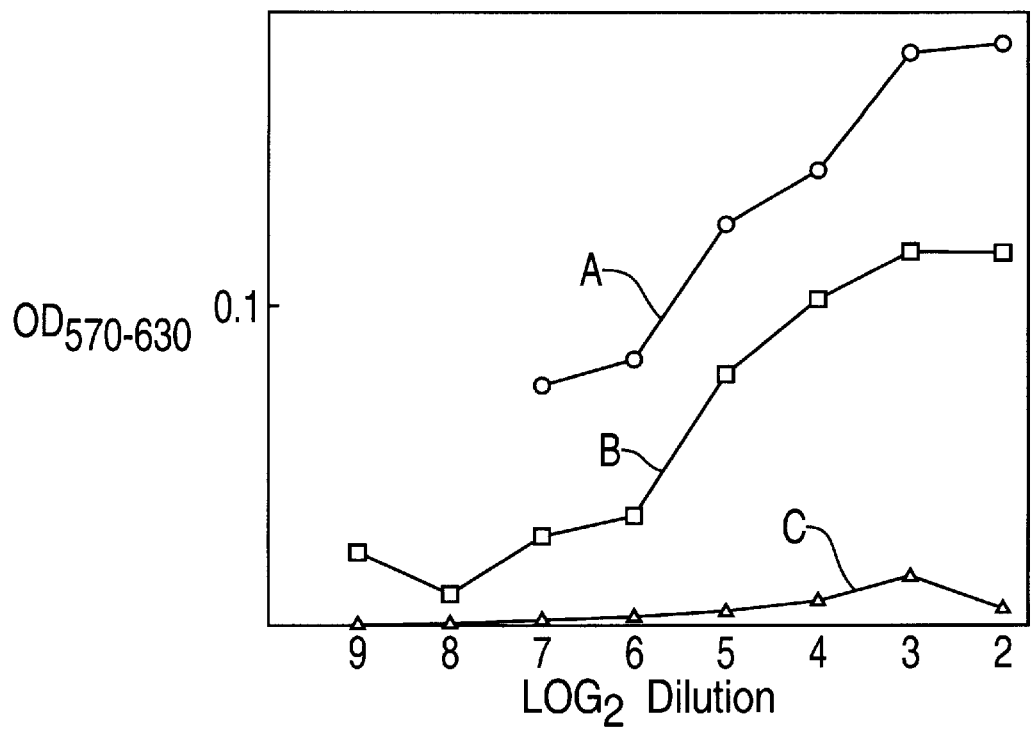
Figure 4C:
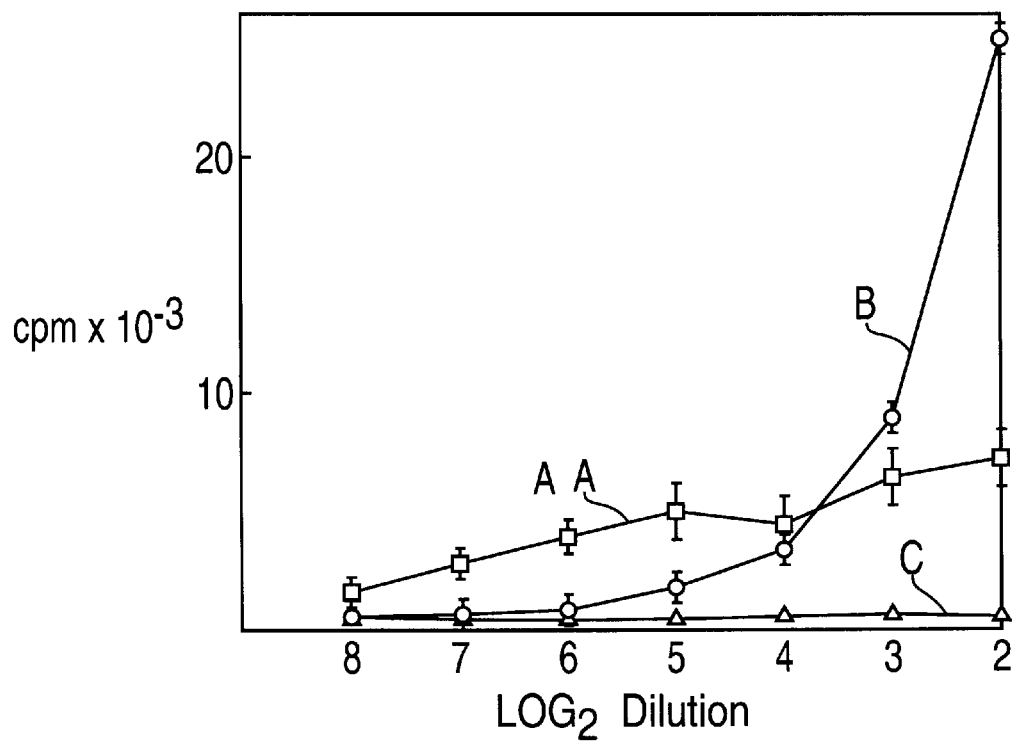

Supernatants from COS cell cultures transfected with the pcD vector containing human cDNA #46 were tested initially for activity on PHA-stimulated human peripheral blood cells, and positive effects were seen. A human T-cell line, JL-EBV that undergoes IL-2 dependent growth after antigen stimulation was utilized for TCGF activity studies. FIG. 4 shows that both T-cell populations responded strongly to human IL-2 and also responded at a lower level to supernatants from COS cells transfected with a human cDNA of the present invention. Whether measured by [$^3$H] thymidine uptake or the MTT colorimetric assay, the slope produced by the polypeptides from the transfected COS cells response curve was less than that of IL-2, and the saturation level of stimulation was half or less of the level seen in response to IL-2.

The original cDNA clone #46 gave a very low titer, and this was improved by expressing the same cDNA clone in L-cells, or by deleting the 36 residue long oligo(dg) stretch in the original clone to produce pcD-125. The vector pcD-125 was formed as follows: pcD-46 was cleaved with Sau3A to isolate a fragment containing the 5' 162 nucleotides of the cDNA insert (eliminating the GC segment) and then the fragment was inserted into the BglII site of p101. The plasmid p101 was derived from pcD-mouse IL-3 (see, Yokota, T. et al. [1984] above) and is deleted for the sequence from the PstI site at the 5' end of the cDNA to a BglII site within the mouse IL-3 cDNA. A BglII site is included at the junction of the deleted sequence. The Sau3A fragment is fused to the SV40 promoter as in pcD-46, except for the GC stretch. The remainder of the human cDNA was then reconstructed with a HindIII-NheI fragment from pcD-46 which carries the 3' end of the cDNA, the SV40 poly A site and all of the pBR322 sequences of pcD-46.

A high expression vector (pEBT178) can be constructed with the plasmid pcD4-RSV-IL3, which carries the mouse IL-3 cDNA in the pcD vector modified in the following way. The SV40 origin fragment is in the reverse orientation, i.e., the late promoter, rather than the early promoter, is in the same orientation as the mouse IL-3 cDNA. A 58bp HindIII-XhoI fragment of the Rous sarcoma virus (RSV) promoter (Gorman, C. et al., Proc. Natl. Acad. Sci. U.S.A. 79:6777–6781 [1982], which is incorporated herein by reference) can be isolated from a variety of sources (e.g., pRSVcat or pRSV-βglobin) which can be modified by converting the HindIII site at the 3' junction of the RSV LTR region to an XhoI site and an upstream NdeI site to an HindIII site. This RSV promoter can be inserted between the SV40 origin and the SV90 splice junctions such that the RSV promoter could transcribe the downstream cDNA. Unique AatII and NdeI sites in this resulting plasmid can be converted to SalI fragment carrying the SV40 origin, the RSV promoter and the cDNA. This SalI fragment can then be inserted into plasmid p201 (Yates, J., et al., Nature 313:812–815 [1985], which is incorporated herein by reference) at the location of the unique ClaI site, which had been converted to a SalI site. The IL-3 cDNA can then be removed by cleaving with XhoI and replaced with the corresponding XhoI fragment containing the human cDNA isolated from pcD-125. The results using pcD-125 suggest that the oligo(dG) segment in pcD-46 is inhibitory to expression of the downstream cDNA insert.

For the following experiments, the human cDNA clone #125 was transfected into COS cells twice, and supernatants obtained (B59-4-125 and B59-5-132). A mock supernatant was prepared with an irrelevant cDNA clone, as described previously.

a) SAC blast assay

As shown in Table I, the SAC preactivated B cells were found to proliferate in response to recombinant IL-2 (produced in *E. Coli*), commercial BCGF (purified from PBL culture stimulated with PHA, obtained from Cytokine Technology International, Buffalo N.Y.) and a T-cell clone (HG-120) supernatant. The transfection supernatants did not significantly stimulate proliferation as measured by thymidine incorporation. These transfection supernatants neither enhanced nor inhibited the proliferation induced by optimal commercial BCGF concentrations.

TABLE II

BCGF ACTIVITY OF THE CLONE #125 TRANSFECTION SUPERNATANTS ON ANTI-$\mu$ PREACTIVATED B CELLS

| % (v/v) of supernatants added | MOCK | B 59-4 125 | B 59-5 132 |
|---|---|---|---|
| | 3HTdR incorporation (c.p.m. = SD) | | |
| 0 | 278 ± 163 | 278 ± 163 | 278 ± 163 |
| 0.2 | 189 ± 64 | 144 ± 65 | 157 ± 28 |
| 1 | 323 ± 44 | 1313 ± 227 | 1078 ± 71 |
| 5 | 408 ± 59 | 4314 ± 231 | 3762 ± 1097 |
| 25 | 397 ± 74 | N.D. | 4289 ± 369 |

Positive controls:
BCGF (25%): 1710 ± 123
Supernatant (25%) of T-cell clone HG-120 activated by ConA (10 μg/ml): 3559 ± 138
IL-2 (10 U/ml) = 1502 ± 414

When tested in combination with optimal concentrations of commercial BCGF, these two transfection supernatants had additional proliferative capacity (see, Table III). The MOCK transfection supernatant had neither stimulatory nor inhibitory activity on the anti $\mu$ preactivated B cells.

TABLE I

ACTIVITY OF THE CLONE #125 TRANSFECTION SUPERNATANTS ON SAC PREACTIVATED B CELLS

Transfection Supernatant Concentration (% v/v)

| | 0 | 0.01 | 0.04 | 0.2 | 1 | 5 | 15 |
|---|---|---|---|---|---|---|---|
| | | | $^3$HTdR incorporation (c.p.m. ≠ SD) | | | | |
| Medium | 2237 ± 487 | | | | | | |
| MOCK | 2237 ± 487 | 1079 ± 67 | 1564 ± 395 | 1789 ± 313 | 40 ± 72 | 1285 ± 62 | 1560 ± 289 |
| MOCK + BCGFc 10% | 12992 ± 2759 | n.d. | 15684 ± 1622 | 13126 ± 2887 | 13714 ± 2014 | 5848 ± 859 | 10128 ± 1703 |
| B 59-4-T25 | 2237 ± 487 | 2086 ± 429 | 861 ± 377 | 2682 ± 1128 | 2374 ± 179 | 2826 ± 526 | 4701 ± 242 |
| B 59-4-125 + BCGFc 10% | 12992 ± 2789 | n.d. | 12655 ± 697 | 5655 ± 280 | 6765 ± 825 | 10023 ± 149 | 10924 ± 506 |
| B 59-5-132 | 2237 ± 487 | 1424 ± 162 | 1328 ± 185 | 1999 ± 56 | 2272 ± 309 | 3493 ± 796 | 3870 ± 668 |
| B 59-5-132 + BCGFc 10% | 12992 ± 2789 | n.d. | 12631 ± 492 | 7203 ± 3212 | 7567 ± 895 | 10119 ± 584 | 12277 ± 1014 |

Controls:
BCGFc (25%): 15869 ± 1039
Gamma IFN 5000 U/ml: 3461 ± 832
IL-2 10 U/ml: 18371 ± 644
ConA 10 82 g/ml: 254 ± 62
PHA 1%: 660 ± 38
Supernatant of clone HG-120 (25%) activated by ConA (10 μg/ml): 8340 ± 784 b) Anti $\mu$ blast activity

The anti $\mu$ preactivated B cells were found to proliferate moderately in response to recombinant IL-2 and commercial BCGF, whereas they strongly proliferated in response to the T-cell clone supernatant and the B-59-4-125 and B-59-5-132 transfection supernatants. The transfection supernatants induced proliferation at concentrations as low as 1% (see, Table II).

TABLE III

THE COMBINED EFFECTS OF COMMERCIAL BCGF AND THE CLONE #125 TRANSFECTION SUPERNATANTS ON ANTI-$\mu$ PREACTIVIATED B CELLS

| % (v/v) SN added | | MOCK | B 59-4 125 | B 59-5 132 |
|---|---|---|---|---|
| | | 3HTdR incorporation (c.p.m. = SD) | | |
| 0 | — | 346 ± 116 | 346 ± 116 | 346 ± 116 |
| BCGF 10% | — | 1835 ± 651 | 1835 ± 651 | 1835 ± 651 |
| " | 0.04 | 1660 ± 304 | 1756 ± 498 | 1911 ± 200 |
| " | 0.2 | 1362 ± 257 | 2303 ± 224 | 2713 ± 158 |
| " | 1 | 1699 ± 160 | 3784 ± 171 | 3507 ± 316 |
| " | 5 | 1518 ± 246 | 7921 ± 217 | 7463 ± 1508 |
| " | 15 | 1093 ± 272 | 8487 ± 1042 | 8389 ± 1060 |

Positive control:
BCGF (25%): 2049 ± 222 c) The effects of the supernatants of COS cells transfected with the human cDNA clone #125 on proliferation of human B cells preactivated by beads coated with anti-$\mu$ antibodies The test was carried out as described above. Briefly, the B cells (>95% pure) were obtained from tonsils and purified by depletion of the T-cells by two rounds of resetting with AET-treated sheep erythrocytes. These B cells were preactivated by anti-$\mu$ antibodies coupled to beads by incubation at 37° C. and 5% $CO_2$ for 24 and 72 hours respectively. After this activation period, the beads were removed by centrifugation over Ficoll-Hypaque and the B cells were washed twice and then seeded at concentrations of $5\times10^4$/flat bottom 0.2 ml well. Transfection supernatants were added at various dilutions. In addition, the activities of commercially available BCGF (25% v/v) and recombinant IL-2 (200 IU/ml) were tested. The B cells preactivated by 24 hours were cultured for 4 days in the presence of the test supernatants (total incubation period 5 days). The B cells preactivated for 72 hours were cultured for 3 days in the presence of the test supernatants (total incubation period 6 days).

The results, shown in Table IV, indicate that the transfection supernatants B-50–4125 and B-59–5132 act both on B cells preactivated for 24 hours and 72 hours, respectively. Significant BCGF activity was observed at concentrations of 0.2% and increased at higher concentrations. Furthermore, commercial BCGF, the supernatant of HG-120, as well as recombinant IL-2, were all found to have BCGF activity.

We investigated whether B cells preactivated with SAC for 72 hours could be induced to proliferate by the human cDNA clone #125 transfection supernatants. The experiment was carried out as described previously with the exception that the B cells were preactivated for 72 hours. In Table V it is shown that B cells preactivated by SAC for 72 hours and cultured for an additional 3 days with the test supernatants do respond. At concentrations of 0.2%, significant proliferation is induced, which increased at higher concentrations of supernatant. Commercial BCGF, the supernatant of T-cell clone HG-120 and recombinant Il-2 are also active in this assay.

TABLE V

THE EFFECTS OF SUPERNATANTS OF COS CELLS TRANSFECTED WITH CLONE #125 ON B CELLS PREACTIVATED BY SAC FOR 72 HRS

| | B cells preactivated | | |
|---|---|---|---|
| % (v/v) supernatant added | MOCK | B 59-4125 | B 59-5132 |
| | 3HTdR incorp. (c.p.m. ± S.D.) | | |
| 0 | | 1621 ± 503 | |
| 0.2 | 1361 ± 377 | 2922 ± 451 | 2874 ± 544 |
| 1 | 1107 ± 250 | 4387 ± 461 | 4544 ± 408 |
| 5 | 1076 ± 104 | 7480 ± 739 | 6933 ± 693 |

TABLE IV

THE EFFECTS OF SUPERNATANTS OF COS7 CELLS TRANSFECTED WITH CLONE #125 ON B CELLS PREACTIVATED WITH ANTI-$\mu$ ANTIBODIES FOR 24 HRS AND 72 HRS RESPECTIVELY

| | B cells preactivated for 24 hrs | | | B cells preactivated for 72 hrs | | |
|---|---|---|---|---|---|---|
| % (v/v) supernatant added | MOCK | B 59-4125 | B 59-5132 | MOCK | B 59-4125 | B 59-5132 |
| | 3HtdR Incorp. c.p.m. ± S.D. | | | 3HTdR Incorp. c.p.m. ± S.D. | | |
| 0 | | 1096 ± 139 | | | 235 ± 67 | |
| 0.2 | 913 ± 180 | 3817 ± 187 | 4147 ± 337 | 149 ± 38 | 546 ± 127 | 419 ± 13 |
| 1 | 900 ± 117 | 5590 ± 392 | 5524 ± 379 | 213 ± 80 | 1790 ± 106 | 1686 ± 117 |
| 5 | 799 ± 153 | 10544 ± 329 | 11154 ± 1145 | 148 ± 38 | 2409 ± 181 | 1931 ± 478 |
| 15 | 1032 ± 296 | 11600 ± 872 | 14486 ± 1827 | 330 ± 90 | 2563 ± 583 | 2691 ± 451 |
| 25 | 2022 ± 1256 | 14687 ± 1133 | 15277 ± 776 | 445 ± 2 | 3863 ± 1473 | 2979 ± 43 | commercial BCGF (25% v/v): 3545 ± 324
supernatant HG-120 (25% v/v): 12451 ± 1273
rec. IL-2 (10 U/ml): 45331 ± 1622 commercial BCGF (25% v/v): 1193 ± 55
sup. HG-120 (25% v/v): 3091 ± 266
IL-2 (10 U/ml): 6997 ± 524

These results indicate that some supernatants from COS cells transfected with plasmids harboring a gene of the present invention induce the proliferation of human B cells preactivated with optimal concentrations of anti-IgM antibodies coupled to beads. These supernatants had additive proliferative capacity with commercial BCGF and do not significantly induce the proliferation of SAC preactivated human B cells. The commercial BCGF preparation contains factors which are different from the factors of the present invention. The data also suggest that different B cell subpopulations or B cells in different stages of activation/differentiation respond to different BCGF's.

d) The effects of the supernatants of COS cells transfected with the human cDNA clone #125 on the proliferation of human B cells preactivated by SAC for 3 days TABLE V-continued THE EFFECTS OF SUPERNATANTS OF COS CELLS TRANSFECTED WITH CLONE #125 ON B CELLS PREACTIVATED BY SAC FOR 72 HRS

| | B cells preactivated | | |
|---|---|---|---|
| % (v/v) supernatant added | MOCK | B 59-4125 | B 59-5132 |
| | 3HTdR incorp. (c.p.m. ± S.D.) | | |
| 15 | 925 ± 149 | 7874 ± 298 | 7422 ± 872 |
| 25 | 1316 ± 250 | 8532 ± 1414 | 9998 ± 1046 | commercial BCGF (25% v/v): 6744 ± 181
sup. HG-120 (25% v/v): 19357 ± 3089
rec. IL-2 (10 U/ml): 17509 ± 1406 e) The effects of supernatants of COS cells transfected with the human cDNA clone #125 non-preactivated human B cells In order to determine whether the transfection supernatants B-59-4-125 and B-59-4-132 had B cell activation activity, their effects were tested on non-preactivated human B cells purified from tonsils.

$1 \times 10^5$ purified B cells (>95% pure) were seeded per 0.2 ml flat bottom well and incubated for 5 days in the presence of the transfection supernatants at various dilutions. The results are shown in Table VI.

TABLE VI

THE EFFECTS OF SUPERNATANTS OF COS CELLS TRANSFECTED WITH CLONE #125 ON NON-PREACTIVATED HUMAN B CELLS

| Source of Supernatant | % (v/v) supernatant added | | | | | |
|---|---|---|---|---|---|---|
| | 0 | 0.04 | 0.2 | 1 | 5 | 15 |
| Medium | 1685 ± 511 | | | | | |
| Mock | | 1388 ± 85 | 1032 ± 139 | 1126 ± 141 | 979 ± 216 | 653 ± 198 |
| B 59-4-125 | | 912 ± 16 | 889 ± 104 | 1081 ± 32 | 1834 ± 223 | 1280 ± 37 |
| B 59-4-132 | | 1250 ± 68 | 929 ± 130 | 1283 ± 124 | 1972 ± 104 | 1620 ± 270 |

BCGFc 25%: 2031 ± 572
PHA 1%: 509 ± 270
Cowan: 60797 ± 2481

The transfection supernatants were not effective in inducing non-preactivated resting human B cell proliferation, indicating that they do not contain B cell activation activity. In addition, commercial BCGF was not effective in the system. The purified B cells responded well to activation by SAC indicating that the negative results with the transfection supernatants could not be attributed to intrinsic non-responsiveness of the B cell preparation.

The results presented here indicate that B cells preactivated with anti-$\mu$ for 24 hours in contrast to B cells preactivated with SAC for 24 hours (as shown previously) showed proliferative responses to the clone #125 transfection supernatants. Furthermore, it is shown that B cells preactivated for 72 hours by SAC also can be induced to proliferate in response to the transfection supernatants. These results suggest that the B cells may have to reach a certain differentiation/activation stage before becoming fully responsive to some polypeptides to the present invention. The human clone #125 gene product does not induce the proliferation of non-preactivated human B cells in this system.

As shown, supernatants from COS cells 25 transfected with plasmids bearing a human cDNA of the present invention induce the proliferation of normal human T-cells and a human T-cell clone, an activity which is similar to human IL-2. However, in the in vitro assays conducted, the maximum extent of proliferation of human T-cells induced in response to the native polypeptides is about half of that induced by human IL-2. The proliferation inducing activity of the polypeptides could not be inhibited by monoclonal antibodies against IL-2 or the IL-2 receptor. These results suggest that the polypeptides can act directly on T-cells (not through the induction of IL-2) and that their activity is not necessarily mediated by the IL-2 receptor. The transfection supernatants also stimulate the proliferation of human B-cells preactivated with optimal concentrations of anti-IgM antibodies coupled to beads and have additive proliferative capacity with a commercial BCGF preparation.

This additive capability, which is typically species specific, is evident when the polypeptides of the present invention are used with other immune-reactive agents; i.e., other agents capable of exerting a response on cells of the immune network. By way of example and not limitation, such polypeptides can exhibit the following activities: (a) minimal effects on colony forming cells (e.g., promotes survival without proliferation) unless other immune-reactive agents are present; (b) in the presence of mouse IL-3, which induces from mouse bone marrow proliferation of some eosinophils, mast cells, macrophages, neutrophils and bursts (colonies of cells containing precursors to erythrocytes, among other cells), the numbers of eosinophils, mast cells, neutrophils, and bursts (size as well) are greatly increased while the number and size of macrophages are decreased; (c) in the presence of mouse G/M-CSF, which induces from mouse bone marrow proliferation of neutrophils, macrophages, eosinophils and some bursts, the numbers of all cell types are greatly increased, except macrophages; (d) in the presence of human G/M-CSF, which induces proliferation from human cord blood of neutrophils, macrophages and eosinophils, macrophage proliferation is diminished, the numbers of neutrophils and eosinophils are increased, and basophils appear in significant amounts; (e) in the presence of mouse G-CSF, which induces proliferation from mouse bone marrow of granulocytes (particularly neutrophils), more and larger colonies of granulocytes are produced; and (f) in the presence of mouse macrophage colony stimulating factor (M-CSF), which induces proliferation from mouse bone marrow of macrophages, less and smaller colonies of macrophages are produced, but the macrophage colonies remaining appear to remain viable.

Thus some of the polypeptides of the present invention are capable of augmenting the activity of various CSF's on progenitor and committed cell lineages, without always altering each of the CSF's activities. This augmenting is typically synergistic, and may only become evident when other immune-reactive agents (e.g., anti-IgM) are also present. The polypeptides can induce the initial proliferation of some hematopoietic cells, but such proliferation may require additional factors to continue.

From the foregoing, it will be appreciated that the cDNA clones of the present invention provide accurate and complete sequence data on a mammalian lymphokine. The invention also provides to those skilled in the art means for producing significant quantities of the factor (essentially free from other hematopoietic factors) for the improved in vitro maintenance of T-cells, granulocytes and mast cells, as well as stimulation of other hematopoietic cells (e.g., B cells, macrophages, etc.). Further, the information gleaned from the cDNA clones increases understanding of the mammalian immune response, enhancing experimental research and therapeutic capabilities.

Although the invention has been described in some detail by way of example for purposes of clarity and understanding, it will be readily apparent to those skilled in the art that certain changes and modifications may be practiced within the scope of the appended claims.

We claim:

1. A method of treating rheumatoid arthritis comprising administering an effective amount of a mammalian interleukin-4.

2. The method of claim 1, wherein said mammalian interleukin-4 is a human interleukin-4.

3. The method of claim 2, wherein said human interleukin-4 is defined by the formula:

His Lys Cys Asp Ile Thr Leu Gln Glu Ile Ile Lys Thr

Leu Asn Ser Leu Thr Glu Gln Lys Thr Leu Cys Thr Glu

Leu Thr Val Thr Asp Ile Phe Ala Ala Ser Lys Asn Thr

Thr Glu Lys Glu Thr Phe Cys Arg Ala Ala Thr Val Leu

Arg Gln Phe Tyr Ser His His Glu Lys Asp Thr Arg Cys

-continued

Leu Gly Ala Thr Ala Gln Gln Phe His Arg His Lys Gln

Leu Ile Arg Phe Leu Lys Arg Leu Asp Arg Asn Leu Trp

Gly Leu Ala Gly Leu Asn Ser Cys Pro Val Lys Glu Ala

Asn Gln Ser Thr Leu Glu Asn Phe Leu Glu Arg Leu Lys

Thr Ile Met Arg Glu Lys Tyr Ser Lys Cys Ser Ser.

4. The method of claim 2, wherein said interleukin-4 exhibits a plurality of activities selected from:

a) a human B cell growth factor activity
b) a human T cell growth factor activity;
c) a human mast cell growth factor activity;
d) a human Ia antigen activity; and
e) a human IgE and IgG1 enhancing activity.

5. The method of claim 4, wherein said interleukin-4 exhibits at least four of said activities.

6. The method of claim 2, wherein said administering is in combination with another immune-reactive agent, including a lymphokine, colony stimulating factor, or immunoglobulin.

7. The method of claim 2, wherein said administering is parenteral.

8. The method of claim 2, wherein said administering is at least 1 µg.

9. The method of claim 2, wherein said human interleukin-4 is expressed from a recombinant nucleic acid.

10. The method of claim 2, wherein said interleukin-4 is substantially pure.

* * * * *